(12) United States Patent
Kim et al.

(10) Patent No.: US 11,589,740 B2
(45) Date of Patent: Feb. 28, 2023

(54) ENDOSCOPE WITH DEPLOYABLE TOOLTIP CAMERA AND METHODS OF USE THEREOF

(71) Applicant: Endopodium, Inc., Escondido, CA (US)

(72) Inventors: Jongwoo Kim, Toronto (CA); Allen Newman, Rancho Santa Fe, CA (US); Thomas Looi, Toronto (CA)

(*) Notice: Subject to any disclaimer, the term of this patent is extended or adjusted under 35 U.S.C. 154(b) by 245 days.

(21) Appl. No.: 16/996,812

(22) Filed: Aug. 18, 2020

(65) Prior Publication Data

US 2021/0127959 A1 May 6, 2021

Related U.S. Application Data

(63) Continuation-in-part of application No. 15/487,381, filed on Apr. 13, 2017, now Pat. No. 10,743,744.

(Continued)

(51) Int. Cl.
| | | |
|---|---|---|
| *A61B 1/05* | (2006.01) | |
| *A61B 1/018* | (2006.01) | |
| *A61B 1/00* | (2006.01) | |
| *A61B 1/06* | (2006.01) | |
| *A61B 1/005* | (2006.01) | |

(52) U.S. Cl.
CPC ............ *A61B 1/053* (2013.01); *A61B 1/0008* (2013.01); *A61B 1/0011* (2013.01); *A61B 1/0016* (2013.01); *A61B 1/0058* (2013.01); *A61B 1/00087* (2013.01); *A61B 1/00114* (2013.01); *A61B 1/00154* (2013.01); *A61B 1/00179* (2013.01); *A61B 1/018* (2013.01); *A61B 1/0684* (2013.01)

(58) Field of Classification Search
CPC . A61B 1/00087; A61B 1/00114; A61B 1/018; A61B 1/0684; A61B 1/0008; A61B 1/00135; A61B 1/00154; A61B 1/00183; A61B 1/0058; A61B 1/0125; A61B 1/00073; A61B 1/0627; A61B 1/07
USPC ........................................................ 600/173
See application file for complete search history.

(56) References Cited

U.S. PATENT DOCUMENTS

| | | | |
|---|---|---|---|
| 2003/0156430 A1* | 8/2003 | Ota ...................... | A61B 1/0669 362/574 |
| 2004/0181138 A1* | 9/2004 | Hindricks .......... | A61B 18/1492 606/41 |

(Continued)

*Primary Examiner* — Aaron B Fairchild
(74) *Attorney, Agent, or Firm* — Davison IP; Scott H. Davison

(57) ABSTRACT

A deployable and flexible tooltip camera is provided for integration within a shaft of an endoscopic tool. The tooltip camera includes a camera mounted to a distal tip of a curved tube which is capable of rotational and translational movement to provide a wide field of view of a tooltip of the endoscopic tool during an endoscopic procedure. The tube retains its curved shape when in use to provide a unique perspective view of the tooltip, but can then be withdrawn into a shaft of the endoscopic tool such that the entire tooltip camera and tube are retained within the shaft of the endoscopic tool and can pass through a cannula. The curved tube may be formed of a super-elastic memory alloy like Nitinol and pre-shaped into an s-curve using a two-step heat treatment process to attain the necessary curvature, and further laser-patterned with holes to attain the necessary flexibility.

13 Claims, 19 Drawing Sheets

Related U.S. Application Data

(60) Provisional application No. 62/322,121, filed on Apr. 13, 2016.

(56) References Cited

U.S. PATENT DOCUMENTS

| | | | |
|---|---|---|---|
| 2006/0149129 A1* | 7/2006 | Watts | A61B 1/0125 600/113 |
| 2008/0021274 A1* | 1/2008 | Bayer | A61B 1/00137 600/117 |
| 2008/0188890 A1* | 8/2008 | Weitzner | A61B 1/04 606/205 |
| 2013/0041214 A1* | 2/2013 | Maahs | A61B 1/0051 600/104 |

* cited by examiner

ENDOSCOPE WITH DEPLOYABLE TOOLTIP CAMERA AND METHODS OF USE THEREOF

CROSS-REFERENCE TO RELATED APPLICATIONS

This application is a Continuation-in-Part of U.S. application Ser. No. 15/487,381, filed Apr. 13, 2017, now U.S. Pat. No. 10,743,744, issued Aug. 18, 2020, the contents of which are incorporated by reference herein in their entirety.

BACKGROUND

Field of the Invention

The embodiments described herein are related to a tooltip camera on an endoscopic tool, and more particularly to a tooltip camera with a deployable and flexible curved shaft.

Related Art

An endoscope is a medical optics device which is used to look inside the human body. It may include a tube known as a cannula which contains optical elements and a light source for capturing images on a distal end of the tube which are viewed by a user outside the body through a monitor or an eyepiece. The endoscope is commonly used for diagnostics and for performing minimally-invasive surgery (MIS), where only small openings are made in the dermis and body walls through which the endoscope is inserted. A user, such as a surgeon performing a medical procedure, will insert the endoscope through an opening in the body, after which the surgeon may insert a medical instrument through another opening with which they can perform the medical procedure while viewing it through the optics in the endoscope.

During the last two decades, MIS has become popular because it offers advantages in terms of less pain, faster recovery, improved cosmesis, and reduced complications. Continuous efforts have been made to improve the morbidity and cosmesis of MIS with a special focus on miniaturization of equipment, the evolution of robotic surgical units, and reduction of port size and number.

Endoscopes are limited by the optics implemented in the endoscope and the resulting ability to clearly view an area within the human body while performing a medical procedure. One example of a laparoscopic procedure is illustrated in FIG. 1, where anywhere from 3 to 5 trocar access ports 502 which are 5 mm to 15 mm in diameter are created into an abdominal cavity 504. When an optical element 506 of an endoscope 508 is inserted separately from the medical instruments 510, it may be difficult to view the medical instrument and the work that is being done. Additionally, manipulating the medical instrument to perform the medical procedure while also manipulating the optical elements to ensure proper viewing of the procedure is often exceedingly difficult, requiring careful manipulation and coordination to move both devices. As shown in FIG. 1, more than one medical instrument 510 may be inserted and may be manipulated simultaneously with the other inserted medical instruments all while continuously repositioning the optical elements of the endoscope for a proper view. Additionally, in cases where the medical instrument must move around an object within the body, such as an organ, tissue, bone, etc., the optical elements of the endoscope may be unable to follow the medical instrument and provide adequate images of an area of interest. The benefits of performing MIS are hampered by the lack of visual and other information available to the surgeon.

As a result of the above issues, a reduced number of ports and small port sizes are preferred. Single port laparoscopic/intrathoracic surgery (SLS) is a rapidly evolving MIS procedure in which surgeons operate exclusively through a single entry. SLS uses a single incision typically from 12 mm to 30 mm in size. Many clinical cases have reported that SLS lowers morbidity associated with the elimination of peripheral ports and leaves only a single small scar compared to the conventional multiport laparoscopic surgery.

It is very demanding to have a small and simple endoscope mechanism with adjustable viewing angles. Due to the confined space and the complexity of single-entry access, there is more obstruction to the field of view (FOV) with SLS. It is important that surgeons monitor end-effectors and the view of their surroundings since surgical procedures with staplers, scissors, or ablation tools are irreversible. The FOV of rigid scopes and their fixed vision are easily obstructed by obstacles in SLS. While efforts have been made to increase visibility in SLS procedures, for example by developing an expandable optical mechanism to create triangulation or offer high articulated motion in the abdominal cavity, there is still a demand for a mechanism to increase visibility in SLS procedures—particularly at the end-effectors.

SUMMARY

Embodiments described herein provide a deployable and flexible tooltip camera integrated within in a shaft of an endoscopic tool for viewing an area around a tooltip during an endoscopic procedure. The tooltip camera includes an image sensor positioned in distal tip of a curved tube fabricated from a shape memory alloy, wherein the tube is capable of rotational and translational movement in order to provide varying viewing angles and a wide field of view of the tooltip and surrounding area during an endoscopic procedure. The shape memory alloy is pre-deformed into the curved shape to provide optimal viewing angles when deployed and to then allow the tube to be fully withdrawn and retained in a shaft of the endoscopic tool via translational movement such that the tube forms a linear shape. The endoscopic tool with the withdrawn tooltip camera is then able to pass through a standard cannula in an endoscope for insertion and removal during an endoscopic procedure.

The tube may be pre-deformed into an s-curve and be fabricated from a shape metal alloy such as nitinol using a two-step heat treatment process to attain the necessary curvature. The tube may also be laser patterned with asymmetric grooves or through-holes to further increase the flexibility and curvature of the tube. At least one wire and an LED-based fiber may pass through the tube and be connected with the image sensor and an LED lighting element to provide power, data transmission and lighting for the image sensing.

In one aspect of the invention, a deployable tooltip camera comprises a hollow shaft with a proximal end and a distal end; and an image capture device disposed within the shaft, the image capture device comprising: a tube fabricated from a shape memory alloy pre-deformed in a substantially curved shape but retaining a substantially linear shape within the shaft; and an image sensor disposed on a distal tip of the tube; wherein a distal portion of the tube is configured to deploy from an opening in the shaft into a deployed position in which the tube assumes the substantially curved shape.

In a further aspect of the invention, a method of viewing an endoscopic tool during an endoscopic procedure comprises the steps of: inserting a distal end of an endoscope into a body cavity, wherein the endoscope is a hollow shaft enclosing an image capture device and the endoscopic tool, and wherein the image capture device comprises: a tube fabricated from a shape memory alloy deformed in a substantially linear shape within the shaft; and an image sensor disposed on a distal tip of the tube; and deploying the image capture device into the body cavity from a distal end of the endoscope, wherein the tube forms a pre-deformed curved shaped upon deployment from the endoscope.

In a yet further aspect of the invention, a method of manufacturing a deployable and flexible image capture device for an endoscope comprises the steps of: forming a hollow tube from a shape memory alloy; laser patterning a distal portion of the shape memory alloy with asymmetrical grooves or through-holes; and heat treating the distal portion of the shape memory alloy to create a curved shape.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Figure 1:
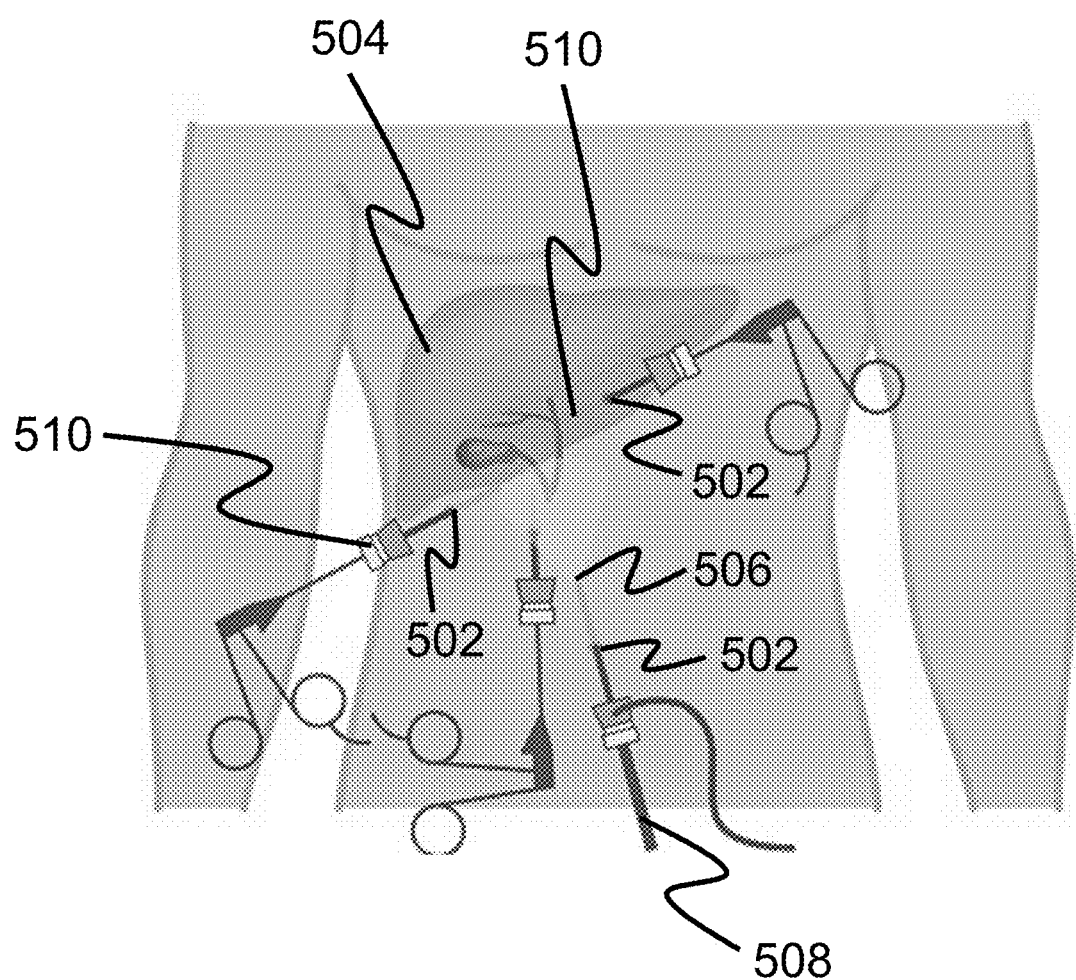
FIG. 1 is an illustration of a laparoscopic procedure utilizing an endoscope and endoscopic tools which are each inserted through separate ports in a body cavity, as is known in the art.

Embodiments described herein provide a deployable and flexible tooltip camera integrated within in a shaft of an endoscopic tool for viewing an area around a tooltip during an endoscopic procedure. The tooltip camera includes an image sensor positioned in distal tip of a curved tube fabricated from a shape memory alloy, wherein the tube is capable of rotational and translational movement in order to provide varying viewing angles and a wide field of view of the tooltip and surrounding area during an endoscopic procedure. The shape memory alloy is pre-deformed into the curved shape to provide optimal viewing angles when deployed and to then allow the tube to be fully withdrawn and retained in a shaft of the endoscopic tool via translational movement such that the tube forms a linear shape. The endoscopic tool with the withdrawn tooltip camera is then able to pass through a standard cannula in an endoscope for insertion and removal during an endoscopic procedure.

Embodiments described herein also provide method of manufacturing the curved tube by pre-deforming the shape memory alloy into an s-curve using a two-step heat treatment process to attain the necessary curvature. The tube may also be laser patterned with asymmetric grooves or through-holes to further increase the flexibility and curvature of the tube. At least one wire and an LED-based fiber may pass through the tube and be connected with the image sensor and an LED lighting element to provide power, data transmission and lighting for the image sensing.

The biggest challenge in developing a flexible and deployable curved mechanism for the needlescopic instrument is the development of a scalable mechanism. The mechanism has to be scalable in terms of manufacturing, assembly, and control. Due to its long and slim structure, their actuators are located at the proximal end and the actuation must be transmitted along their shaft to an end-effector at the distal end. Most of the instruments use tendon-pulley mechanisms for transmission. In addition, researchers used magnetic control, fluidic actuators, smart materials, etc. However, due to routing and tensioning, assembling tendons becomes more difficult with an increasing number of actuators and decreasing sizes. The length of its moment arm becomes too short to provide enough moment. Complicated structures with many actuators are costly and its assembly are challenging.

To solve many of these issues, a scalable and deployable "bending wrist" tube was developed to allow for an extended range field of view (FOV) and adjustment of the viewing angle in microsurgical procedures. In one embodiment, the proposed mechanism utilizes an s-curved nitinol (Ni—Ti) tube with two degrees of freedom (DOF). The nitinol tube may be laser patterned anisotropically to shape a high curvature so that it keeps a small motion envelope. The mechanism incorporates a camera on a deployable arm structure to the tip of the endoscopic tool. When stored, the mechanism is retracted in the shaft of the laparoscopic tool thanks to the super-elasticity of nitinol. When deployed, the mechanism pops up laterally to expose the camera pointing at the tooltip. When it advances further, the wrist starts bending caused by repulsive force from the edge of the main shaft's hole pattern. The bending can be controlled by the wrist's translational displacement. The tooltip camera is scalable and able to be straightened to pass through a small diameter trocar and then deployed in a curved shape for optimal viewing of the endoscopic procedure.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Endoscope Assembly with Tooltip Camera

Figure 2:
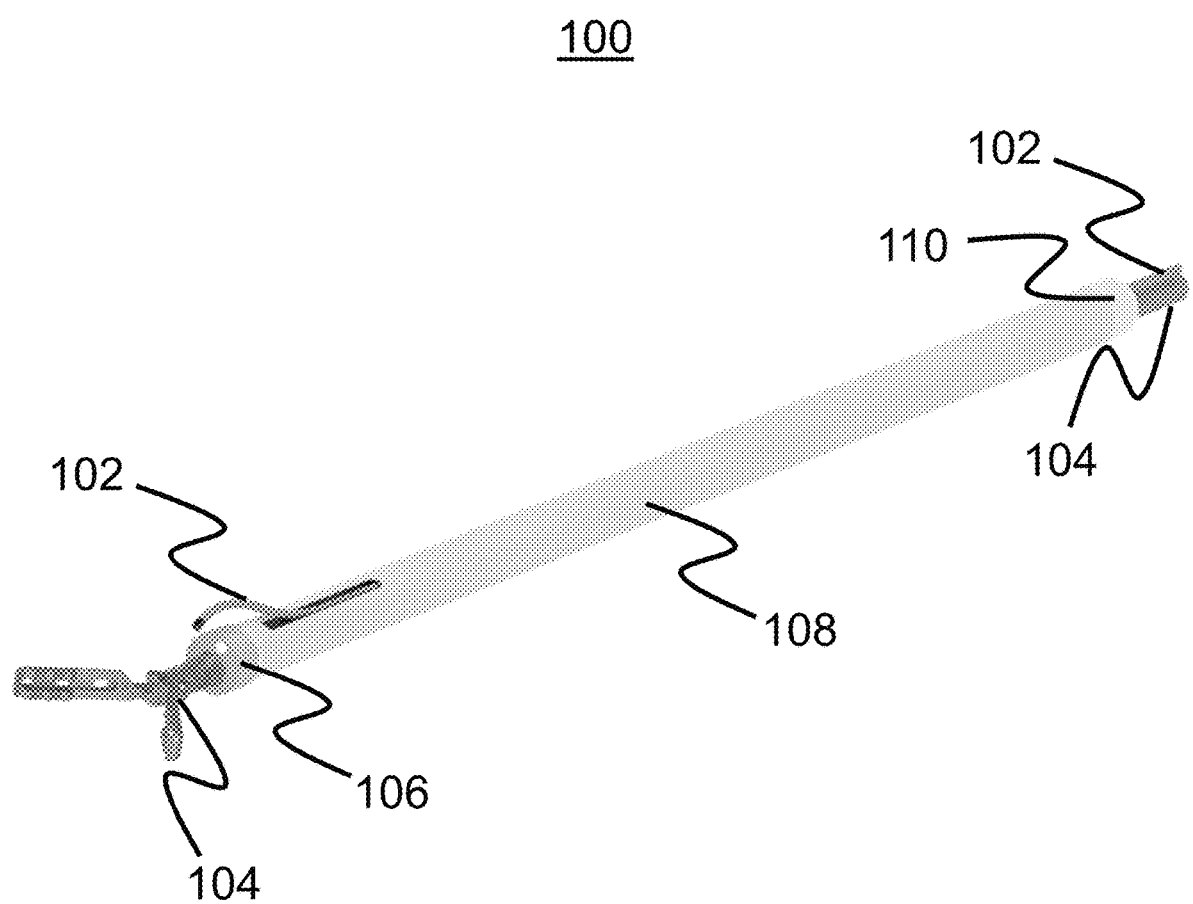
FIG. 2 is an illustration of an endoscope with a deployable tooltip camera and endoscopic tool, according to an embodiment of the invention.

FIG. 2 is an illustration of one embodiment of an endoscope 100 with a deployable tooltip camera 102 and endoscopic tool 104 extending from a distal end 106 of a hollow shaft 108. The tooltip camera 102 and tool 104 extend through the length of the shaft 108 and exit from a proximal end 110 of the shaft, where they can be connected with control mechanisms to independently control each component. Additionally, the tooltip camera 102 may also be connected with a computing device and monitor to display the images captured by the camera.

Figure 3:
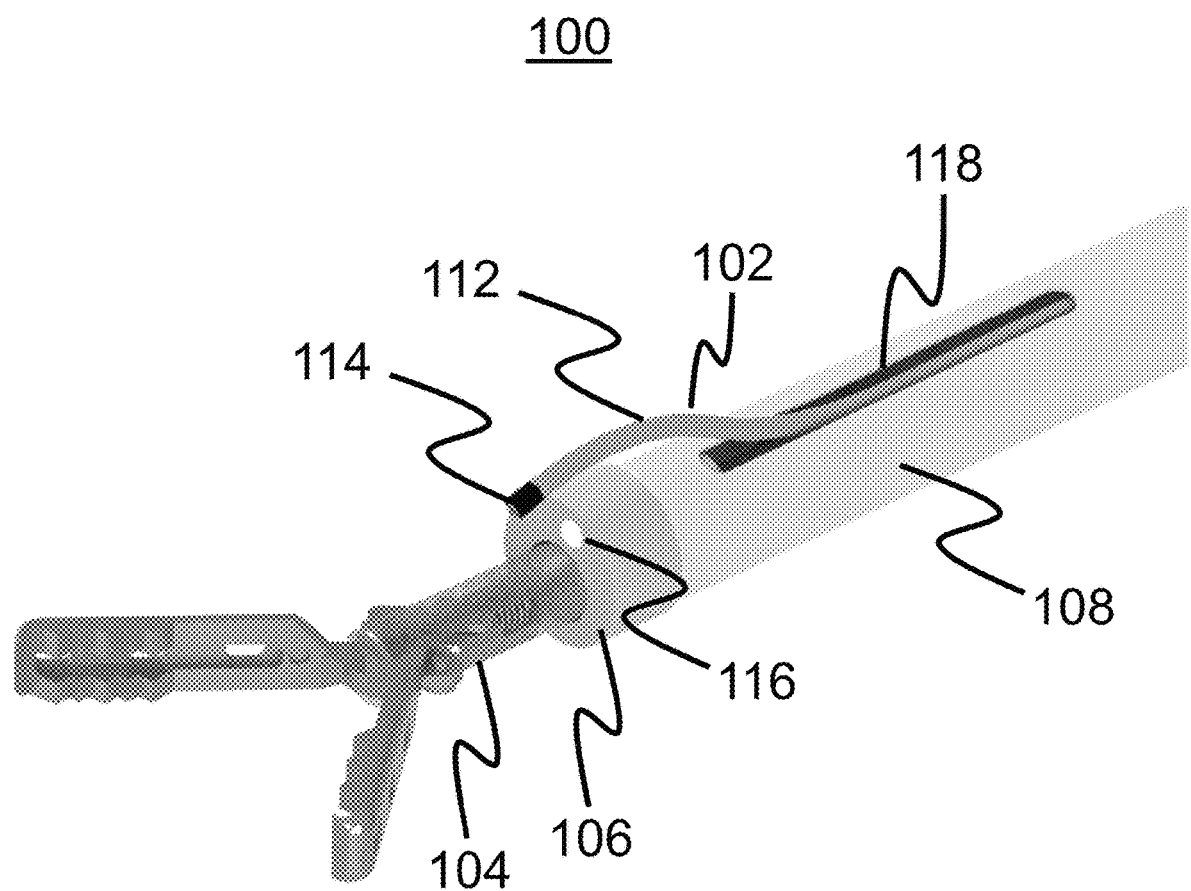
FIG. 3 is an illustration of a distal end of the endoscope, according to one embodiment of the invention.

FIG. 3 is a close-up view of the distal end 106 of the endoscope 100 more clearly illustrating the components of the tooltip camera 102, which includes a tube 112 with an image sensor 114 disposed on a distal tip. An additional lighting element 116 may be disposed on the distal end 106 to illuminate the tool 104 and surrounding area. One or more wires (see FIG. 10) may be disposed within the tube 112 to connect the image sensor 114 with a power source and image processor or display outside of the body cavity adjacent with the proximal end 110 of the shaft 108. In this embodiment, the tooltip camera extends from a slot-like opening 118 disposed in a side portion of the shaft immediately proximate to the distal end 106.

Figure 4:
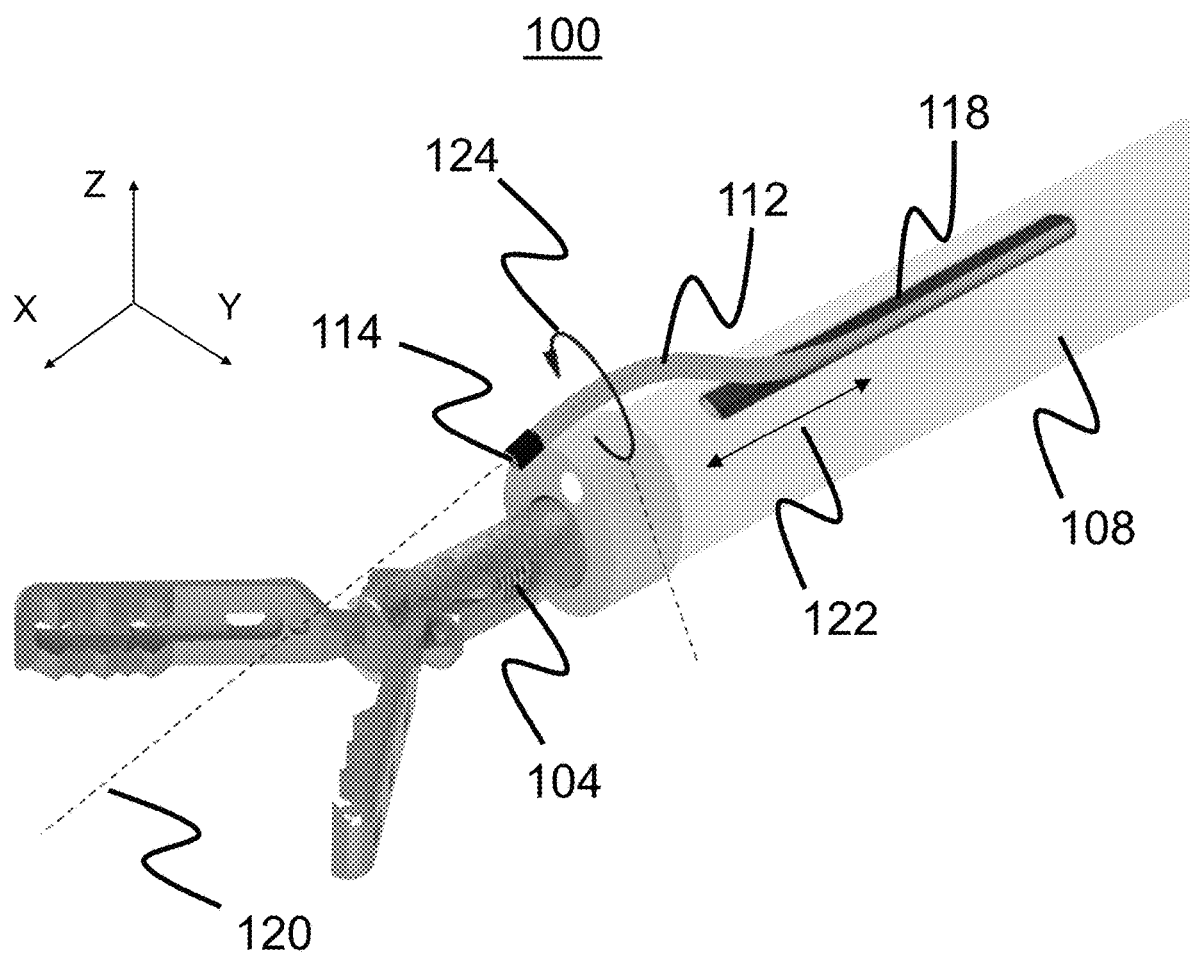
FIG. 4 is an illustration of degrees of freedom and a viewing angle of the tooltip camera, according to one embodiment of the invention.

The tube 112 has a generally curved shape such that the tube initially extends out of and away from the opening 116 before curving back toward the shaft 108 such that the image sensor 114 at the distal tip is positioned generally above and behind the tool 104 while being pointed at the tool 104. FIG. 4 illustrates a directional line 120 representing the direction in which the image sensor 114 is pointed. Furthermore, the tube 112 is capable of both translational movement along an x-axis, represented by the directional arrow 122, and rotational movement about the x-axis, represented by the circular arrow 124. An axis diagram illustrating the x, y and z axes is provided for reference. The translational movement 122 allows the tooltip camera 102 to not only extend from the opening 118 but also to position the image sensor at any point along the x-axis, whether proximal or distal to the illustrated position in FIGS. 2-4 (see FIGS. 22A-22D, below).

Instead of complicated structures and many actuators, the 2-DOF movement of the s-curved nitinol tube can adjust the FOV, leading to a simple, intuitive, and scalable structure. The arm has translational and rotational movement along the x-axis as shown in FIG. 4. The camera is located at the distal tip of the tube. The arm's rotational movement rotates the direction of the camera about x-axis and the translational movement changes the x-coordinate of the camera. Once the arm advances further and has reached the edge of the main shaft's hole pattern, the repulsive force from the edge uplifts the arm. The translational advancement along +x-axis allows the arm to function as a bending wrist. The degree of translational advancement determines the bending degree of the continuum arm according to the arm's bending stiffness, $EI_{arm}$. The pitch angle of the camera's direction is the function of the translational displacement, $\delta_x$, and $EI_{arm}$ $$\text{pitch angle} = f(\delta_x, EI_{arm}) \quad (1)$$

The roll angle of the camera's direction is determined by the arm's rotational angle about the x-axis, $\omega$. The upper and lower constraints of the rotational angle is determined by the width of the hole pattern of the main shaft, $L_w$. Considering its geometry, the boundary relation is given as (3) where $r_{arm}$, $r_{main}$ are the radius of the arm and the main shaft, respectively.

$$\text{roll angle} = g(\omega) \quad (2)$$

$$-\sin^{-1}\left(\frac{L_w}{2}\right) + \tan^{-1}\left(\frac{r_{arm}}{r_{main}}\right) \leq \omega \leq \sin^{-1}\left(\frac{L_w}{2}\right) - \tan^{-1}\left(\frac{r_{arm}}{r_{main}}\right) \quad (3)$$

The translational movement also offers the reversible deployment of the arm from the main shaft. The translational movement along the negative x-axis retracted the deployable arm into the main shaft. The deployable arm of nitinol is straightened when it is fully retracted into the main shaft thanks to the super-elasticity of nitinol. When popped out again, the arm restores its s-shape structure.

The control of the FOV can be generated by combining rotation and translation movements of the deployable arm. The camera's direction can be represented by rotation about z-axis by $\omega$ and the rotation about y axis by $f(\delta x, EI_{arm})$ as (4) and (5). It is difficult to have analytical solution of (1) since it is continuum bending wrist with micro patterning. The relationship of (1) is studied in section III, and then the camera direction can be controlled by (5).

$$\vec{V}_{cam} = \vec{V}_{cam,i} Rot(z, \omega) Rot(y, f(\delta_x, EI_{arm})) \quad (4)$$

$$\vec{V}_{cam} = \begin{bmatrix} \cos 10.58° & 0 \\ 0 & 1 \\ -\sin 10.58° & 0 \end{bmatrix} \begin{bmatrix} \cos\omega & -\sin\omega & 0 \\ \sin\omega & \cos\omega & 0 \\ 0 & 0 & 1 \end{bmatrix} Rot(y, f(\delta_x, EI_{arm})) \quad (5)$$

Figure 5A:
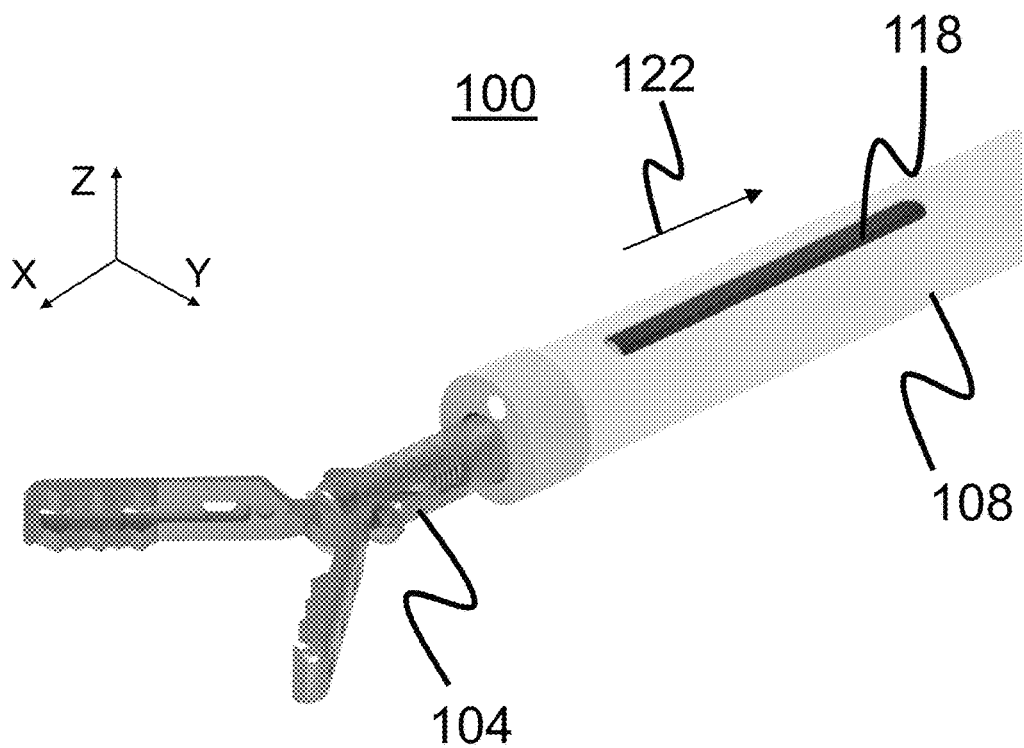
FIG. 5A is an illustration of the tooltip camera in a non-deployed position, according to one embodiment of the invention.
Figure 5B:
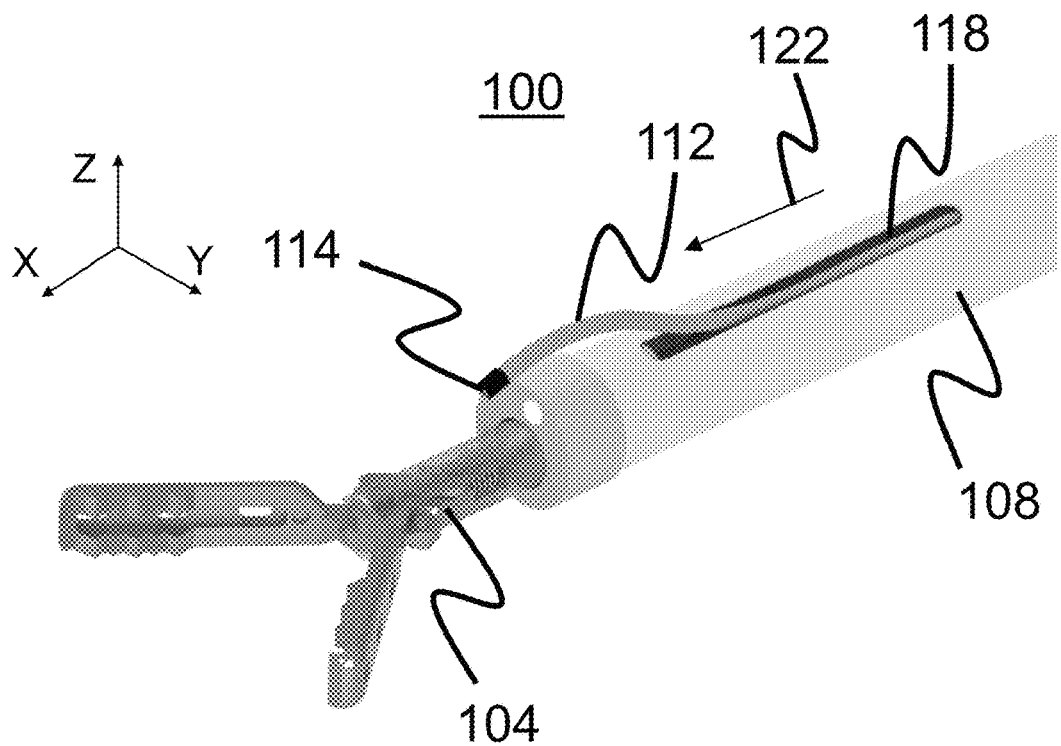
FIG. 5B is an illustration of the tooltip camera in a deployed position, according to one embodiment of the invention.

FIG. 5A illustrates a withdrawn position of the tooltip camera 102 where the camera 102 is completely enclosed within the shaft 108. FIG. 5B illustrates a deployed position of the tooltip camera 102 where the camera 102 has been translated along the x-axis such that the image sensor is directed at the tool 104.

To achieve the curved tube shape in the deployed position while allowing the tube to retract into the linear-shaped tube, the tube 112 may be fabricated from a shape memory alloy, which allows the curved shape of the tube 112 in the deployed position to deform into a substantially linear shape as it is withdrawn into the shaft 108. A shape memory alloy such as nitinol provides a shape memory and super-elasticity which allows the tube to be formed into the curved shape and deformed into a linear or other shape. Nitinol alloy has the additional advantage of being biocompatible, making it ideal for use in medical procedures. The tube may be fabricated such that the curved shape is the pre-deformed shape which the tube will revert to when no other forces are applied to the tube, while the deformed shape is a substantially linear shape which the tube deforms into as it is withdrawn from the deployed position into the withdrawn position.

Figure 6A:
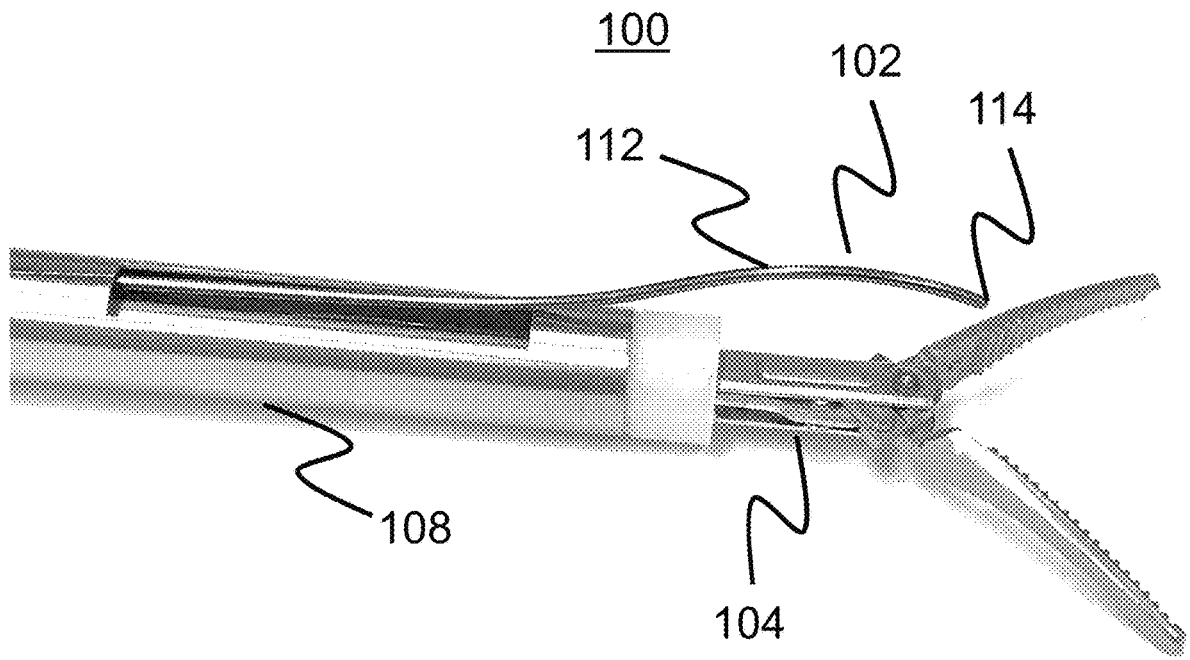
FIG. 6A is a side perspective view image of the endoscope with the tooltip camera in a deployed position, according to one embodiment of the invention.
Figure 6B:
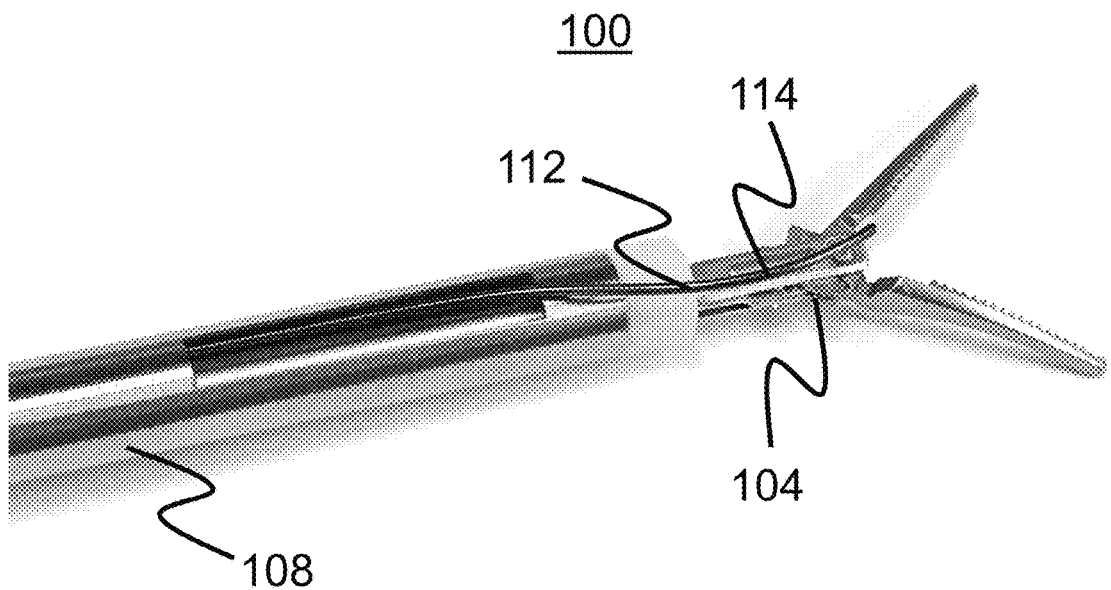
FIG. 6B is a side perspective view image of the endoscope with the tooltip camera in a deployed and rotated position, according to one embodiment of the invention.

FIG. 6A and FIG. 6B are images of the endoscope 100 which illustrate the ability of the tooltip camera 102 to move about the x-axis and provide a second degree of freedom to further widen a field of view of the image sensor 114. In FIG. 6A, the tooltip camera 102 is in a first deployed position. By rotating the tube 112 about the x-axis, the tube can be rotated in either a clockwise or counter-clockwise direction to adjust the viewing angle of the image sensor. FIG. 6B therefore shows the tube 112 in a second deployed position where the tube 112 has been rotated in a clockwise direction (as viewed from the proximal end of the endoscope) to provide an additional field of view (FOV) of the tool and surrounding area.

Figure 7:
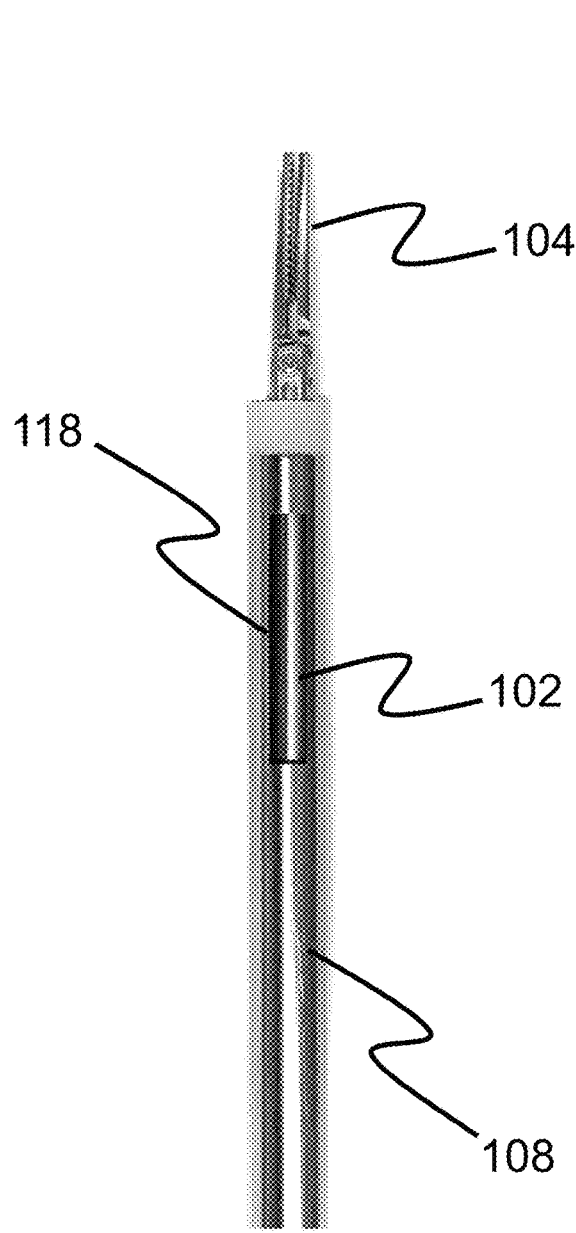
FIG. 7 is a top-down view image of the endoscope with the tooltip camera in a non-deployed position, according to one embodiment of the invention.

FIG. 7 is a top-down view image of the endoscope with the tooltip camera 102 in the withdrawn position, illustrating how the tooltip camera 102 can be entirely contained within the shaft 108 of the endoscope 100. During an endoscopic procedure, the endoscope may be inserted into a body cavity in this withdrawn position, which may also include having the tool 104 also withdrawn into the shaft 108. Once at least a distal portion of the endoscope is inside the body cavity, the tooltip camera 102 and tool 104 may be deployed from the endoscope shaft, as described above. In a laparoscopic procedure such as that illustrated in FIG. 1, the endoscope 100 may be inserted through a cannula, which is a hollow shaft inserted through a body cavity wall during minimally-invasive surgery (MIS) to maintain the opening during the procedure. In either situation, the tooltip camera 102 must be completely retained within the endoscope shaft 108 to allow for insertion into the body cavity.

Figure 8:
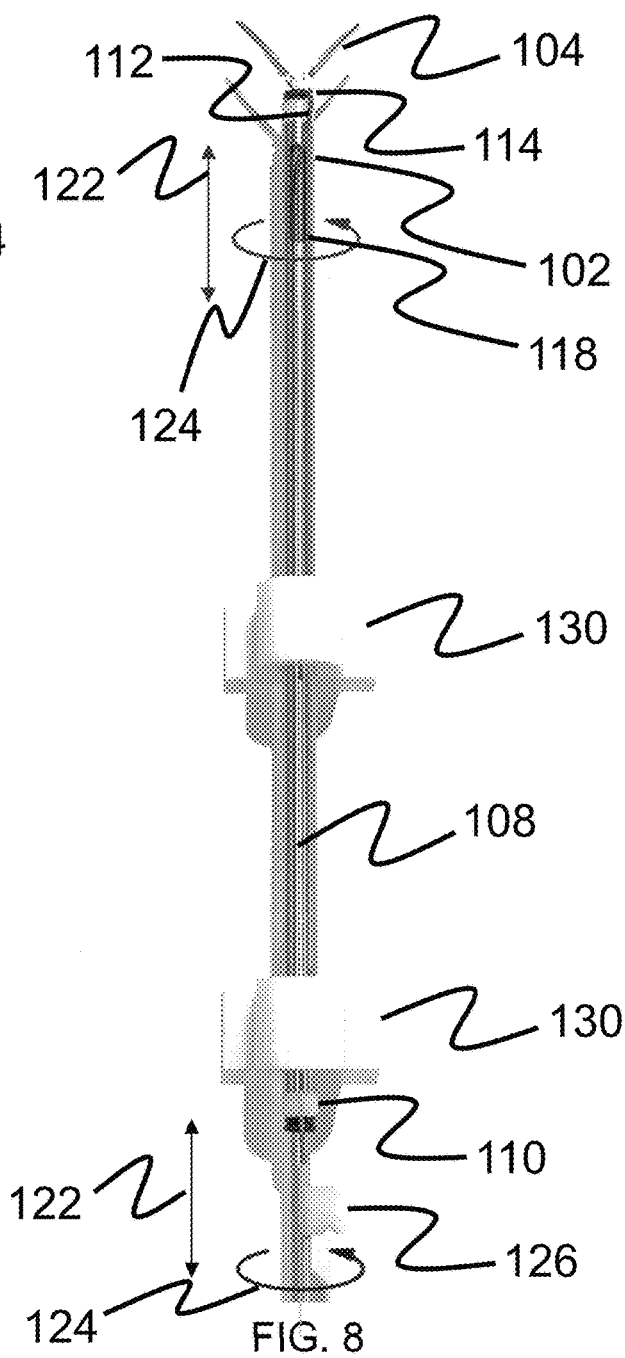
FIG. 8 is a top-down view image of the endoscope showing a control mechanism for the tooltip camera, according to one embodiment of the invention.

FIG. 8 is a top-down view image of the endoscope 100 showing a control mechanism 126 for both translating and rotating the tooltip camera 102 along and about the x-axis 122, respectively. In this embodiment, the control mechanism 126 may be a tab attached with the tube 112 adjacent the proximal end 110 of the endoscope where the tube 112 exits the endoscope shaft 108. Securing mounts 130 are provided to secure the endoscope in a fixed position for demonstrating the movement of the camera 102 relative to the endoscope shaft 108. The tab is attached with a sheath which surrounds and is attached with the tube 112 such that movement of the tab along the x-axis 122 or about the x-axis 124 results in identical movement of the tube 112. Thus, the control mechanism 126 may be utilized to deploy the tooltip camera 102 from the withdrawn position into the deployed position (or any position in between), as well as to rotate the tube 112 and image sensor 114 about the x-axis 124.

Figure 9:
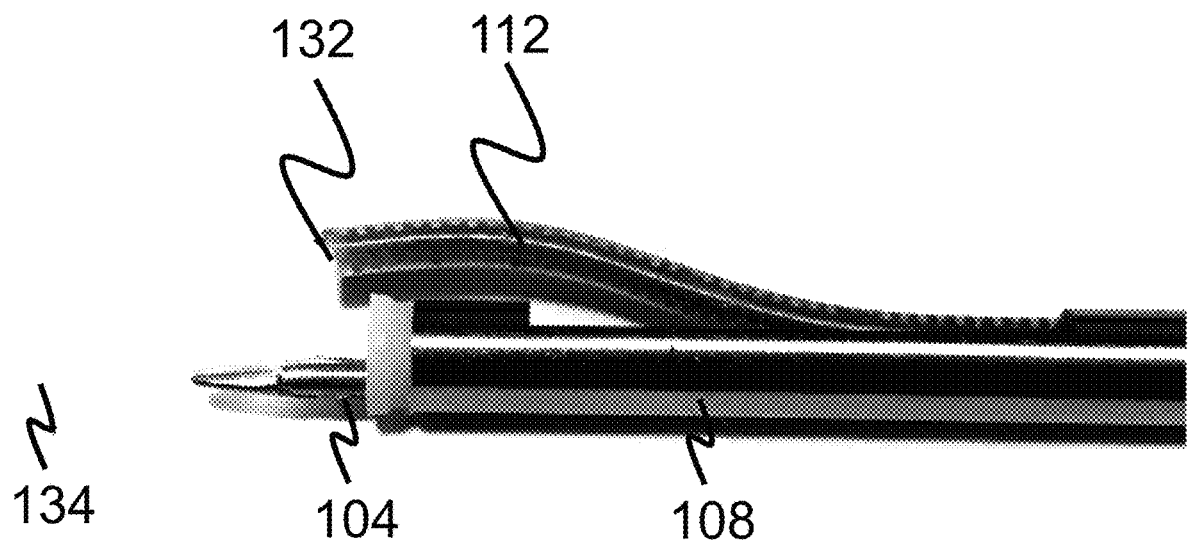
FIG. 9 is a side view image of the endoscope with the tooltip camera in a deployed position, according to one embodiment of the invention.

FIG. 9 is a side view image of the endoscope 100 with the tooltip camera 102 in the deployed position above the endoscope shaft 108. In this embodiment, the tooltip camera 102 also includes a lighting element 132 on the distal tip of the tube adjacent the image sensor 114 in order to provide more direct lighting of the area immediately in front of the image sensor 114. The bright area in front of the tool 104 illustrates an area 134 illuminated by the lighting element 132. The lighting element may be an LED powered by a fiber running through the tube 112, and an Ultrahigh NA fiber (NA>0.82) may be used to match the high FOV of the lens.

Figure 10:
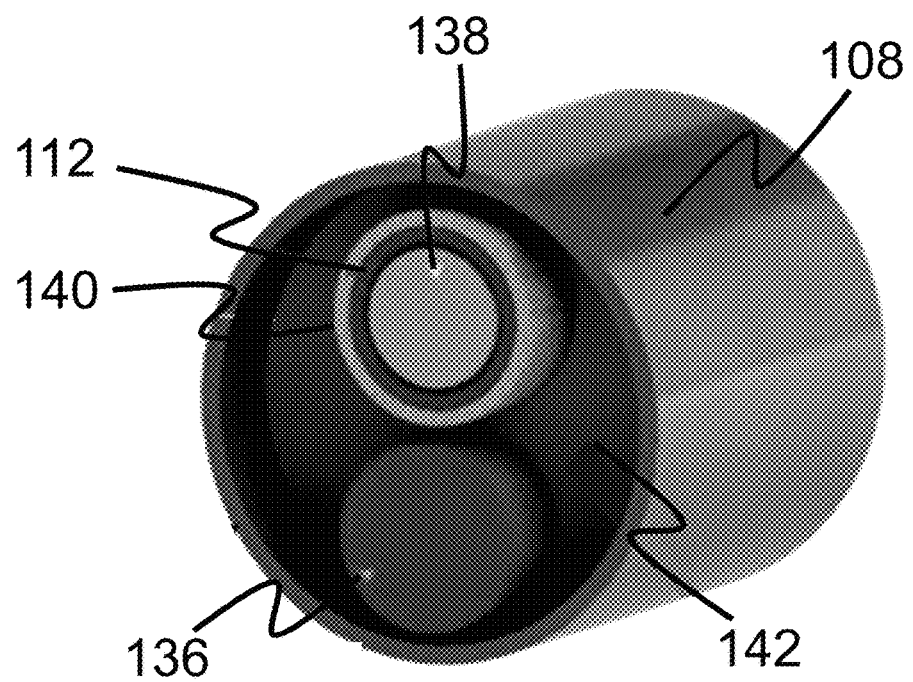
FIG. 10 is a cross-sectional view illustration of a shaft of the endoscope, according to one embodiment of the invention.

FIG. 10 is a cross-sectional view illustration of the endoscope shaft 108 at a mid-point along the shaft prior to the opening 118 where the tooltip camera 102 is deployed. In this embodiment, the main shaft 108 contains the deployable patterned tube 112 with a coating and surgical instrument (tool 104). A tool shaft 136 is shown on a lower portion of the endoscope shaft 108 and connects the tool 102 with a control mechanism (not shown) adjacent the proximal end of the endoscope, similarly to the control mechanism illustrated in FIG. 8. The cross-section of the tube 112 illustrates how tooltip camera 102 includes a wire 138 disposed within the tube 112 to connect the image sensor 114 with an image processor or display. The endoscopic camera (minnieScope-XS ENA-10005-AS, EC3-L04-F5-T1, Enable, Inc., CA, USA) passes through the hollow space of the tube and is connected to a power source, and its CMOS sensor is located at the distal tip of the tube 112. In one embodiment, the camera has 120 degrees of FOV lens with depth of field 2.5 mm-70 mm. The CMOS sensor has 1 M pixel resolution and 1.40 mm of the outer diameter and its electric cable thickness is 1.20 mm.

The tube 112 surrounds the wire 138, and, in this embodiment, is coated with polytetrafluoroethylene (PTFE). The PTFE coating is heat-shrunk around the patterned portion of the tube (2:1 shrink ratio, AWG 17, Zeus, USA) and reduces the friction between the tube 112 and the shaft 108, while additionally serving to conceal the through-hole patterning on the distal portion of the tube 112. The coating lowers friction between shafts and conceals the through-hole patterns of the wrist. In order to secure the tool shaft 136 and tube 112 within the endoscope shaft 108 and prevent unnecessary movement or friction, a housing 142 may be disposed within the shaft 108.

FIG. 9 demonstrates the assembly when a 2 mm-diameter end effector is utilized. The centers of the camera and end effector lie on the vertical line that passes the center of the main shaft. The curved-shape's center is located approximately 0.95 mm higher in the z-axis from the center of the main shaft. The tooltip camera can also be integrated into commercial surgical instruments. According to the diameter of the instrument, a 5 mm or 8 mm-diameter main shaft may be employed to assemble the surgical instrument and deployable endoscope arm.

Figure 11A:
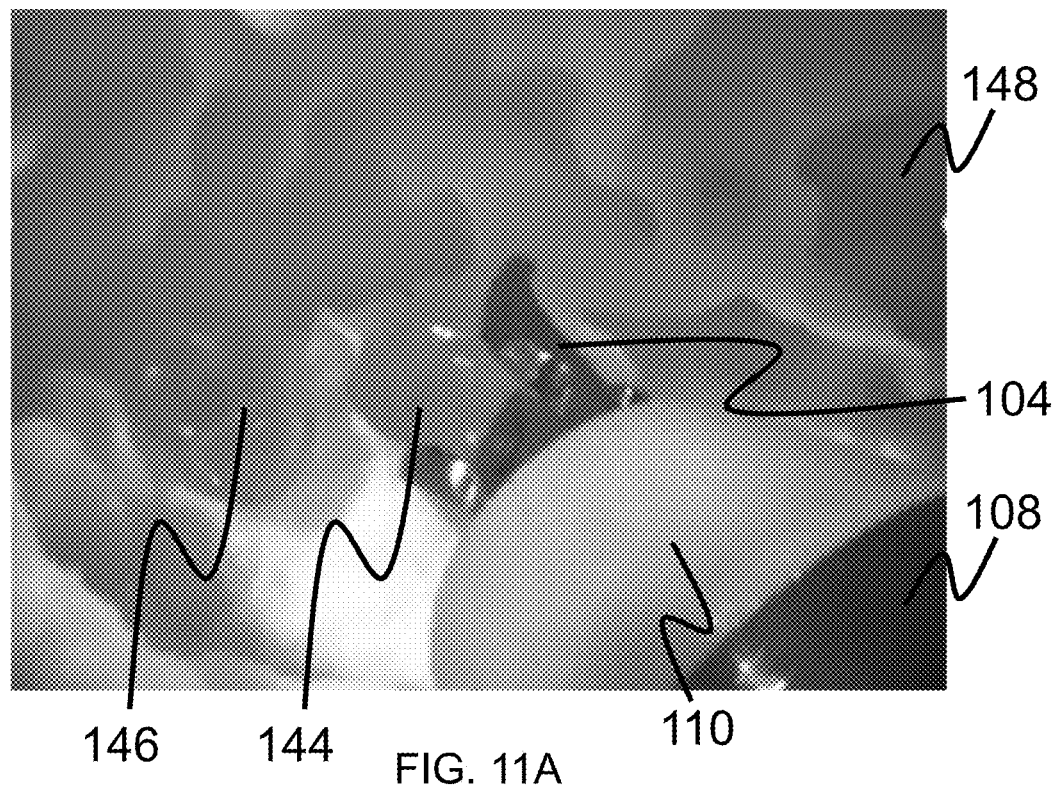
FIG. 11A is a right-side rear perspective view image captured by the tooltip camera after clockwise rotation about an x-axis, according to one embodiment of the invention.
Figure 11B:
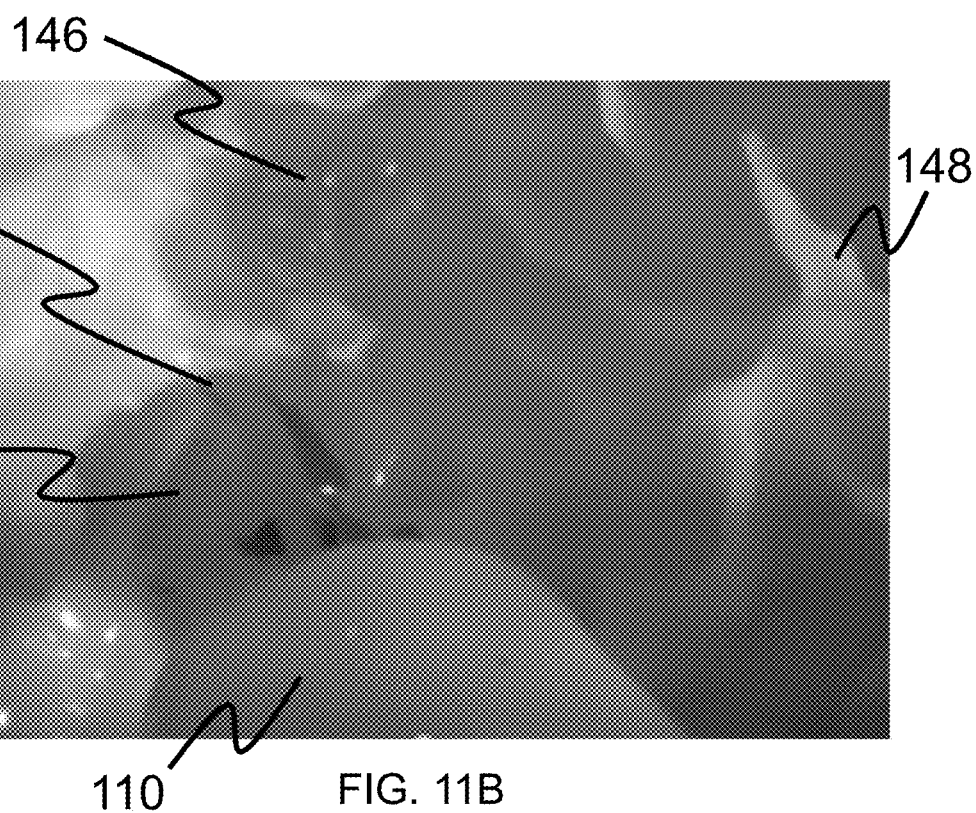
FIG. 11B is a left-side rear perspective view image captured by the tooltip camera after counter-clockwise rotation about the x-axis, according to one embodiment of the invention.

Images illustrating the differing fields of view (FOV) provided by the translation and rotation of the tooltip camera are shown in FIG. 11A-12B. The assembly illustrated herein includes laparoscopic graspers and scissors which are 5 mm and 1.9 mm in diameter. FIG. 11A is a right-side rear perspective view image captured by the tooltip camera after clockwise rotation about the x-axis, which provides one view of the tool 104 and distal end 106 of the shaft 108 as it grasps a first object 144 while avoiding a second object 146 and surrounding tissue 148. FIG. 11B is a left-side rear perspective view image captured by the tooltip camera after counter-clockwise rotation about the x-axis, which provides a different view of the tool 104 as it grasps the first object 144 while avoiding the second object 146. The images illustrate how the tooltip camera can be rotated about the x-axis to ensure that the tool is grasping the correct object and not any adjacent objects or surrounding tissue.

Figure 12A:
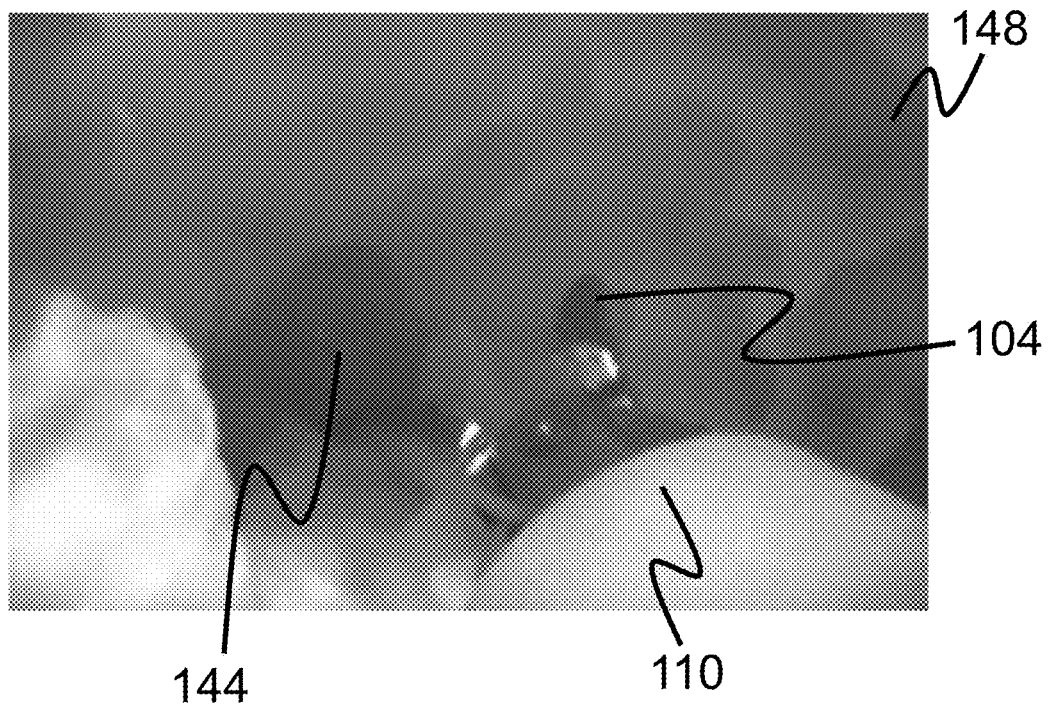
FIG. 12A is a rear perspective view image captured by the tooltip camera in a proximal position along an x-axis of the endoscope shaft, according to one embodiment of the invention.
Figure 12B:
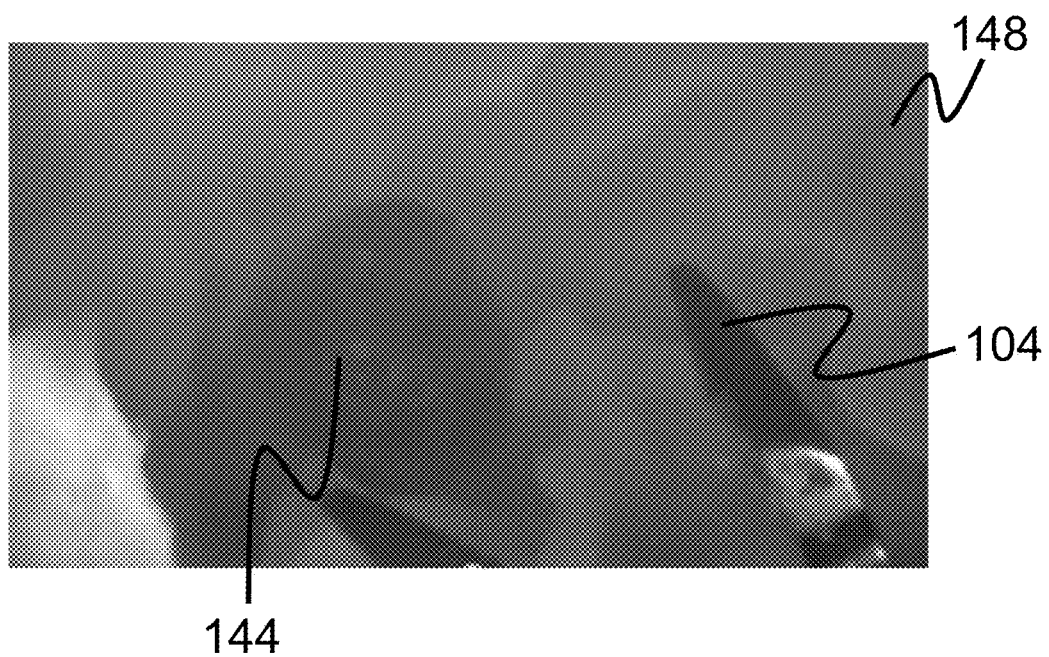
FIG. 12B is a rear perspective view image captured by the tooltip camera in a distal position along the x-axis of the endoscope shaft, according to one embodiment of the invention.

Similarly, FIG. 12A is a rear perspective view image captured by the tooltip camera in a first, proximal position along an x-axis of the endoscope shaft, illustrating the tool 104 as it approaches the first object 144 and surrounding tissue. In FIG. 12B, the tooltip camera has been translated along the x-axis to a second, distal position closer to the tool 104 and first object 144, providing a better view of the tool 104. The images illustrate how the tooltip camera can be translated along the x-axis to ensure that the tool is grasping the correct object and not any of the surrounding tissue.

Methods of Use

Figure 13:
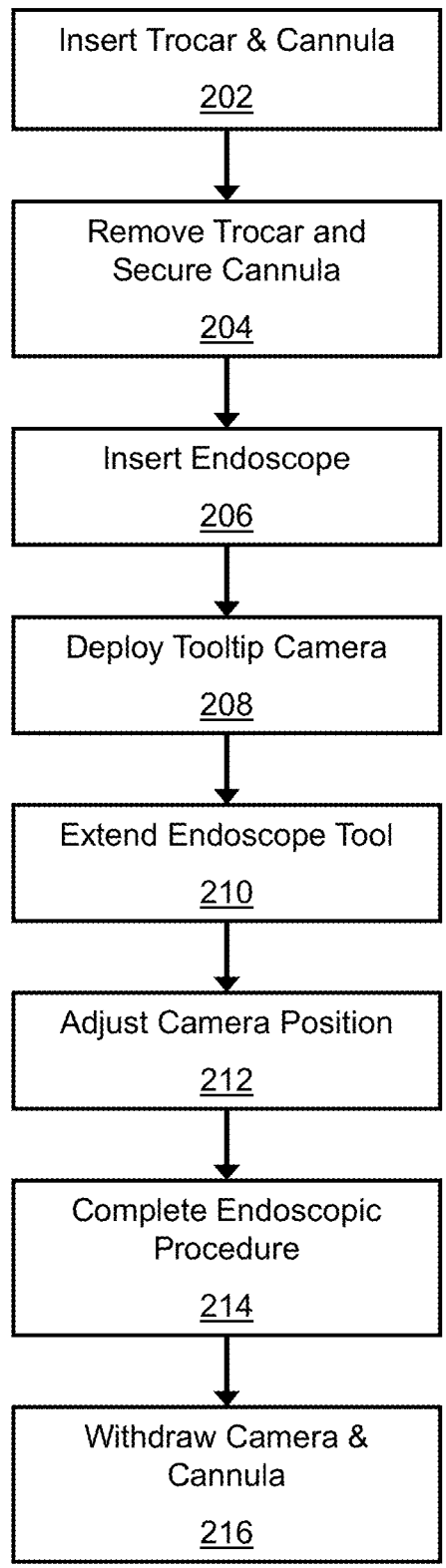
FIG. 13 is a flow diagram illustrating an example process for performing an endoscopic procedure with the tooltip camera and endoscopic tool, according to one embodiment of the invention.

FIG. 13 is a flow diagram illustrating an example process for performing a single port laparoscopic surgery (SLS) procedure with the endoscope where the endoscope is to be inserted through a cannula in an incision in an abdominal wall. In step 202, a trocar and cannula are inserted through a body cavity wall to create an opening for the endoscope. In step 204, the trocar is removed and the cannula remains to maintain the opening during the procedure. The endoscope is then inserted through the cannula in step 206 until a distal portion of the endoscope is disposed in the body cavity. In step 208, the tooltip camera is deployed via translation along the x-axis. The endoscopic tool is deployed from the tip of the endoscope in step 210. In step 212, the tooltip camera can then be adjusted along or about the x-axis to provide any needed view of the tool and surrounding area in the body cavity while the endoscopic procedure is completed in step 214. Once complete, in step 216, the tooltip camera is withdrawn back into the shaft of the endoscope and the endoscope can be removed from the cannula.

It is noted that a method for performing a more general endoscopic procedure through insertion of the endoscope into an existing body cavity opening would simply not require the steps of making an incision and first inserting a trocar and cannula. Additionally, while the laparoscopic procedure described above refers to the insertion of the endoscope into a body cavity, additional SLS endoscopic procedures may be performed in different areas of the body where a body cavity is not present. For example, the endoscope could be utilized for a neurosurgical procedure by inserting the endoscope into the brain, since the endoscope can provide a viewing area around the tool with the tooltip camera extended only a small distance from the endoscope. Similarly, a biopsy could be performed on an area of the body consisting primarily of musculature or dense tissue that would otherwise be impractical for a standard laparoscopic procedure requiring multiple different ports for viewing and accessing an area.

Fabrication of the Tooltip Camera

Figure 14:
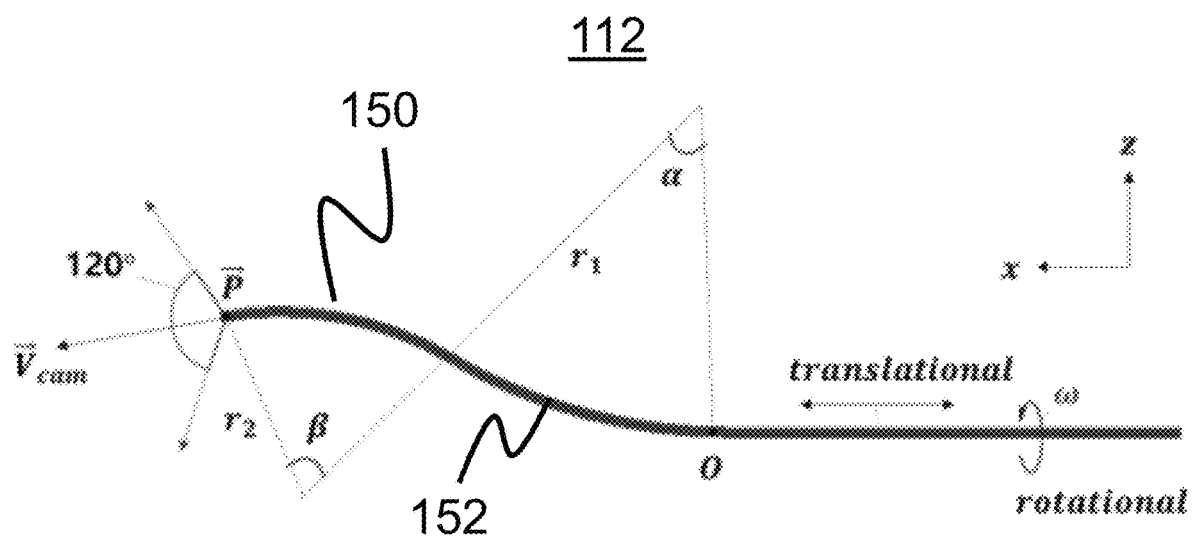
FIG. 14 is an illustration of a tube of the tooltip camera pre-deformed into an s-shape curve, according to one embodiment of the invention.
Figure 15:
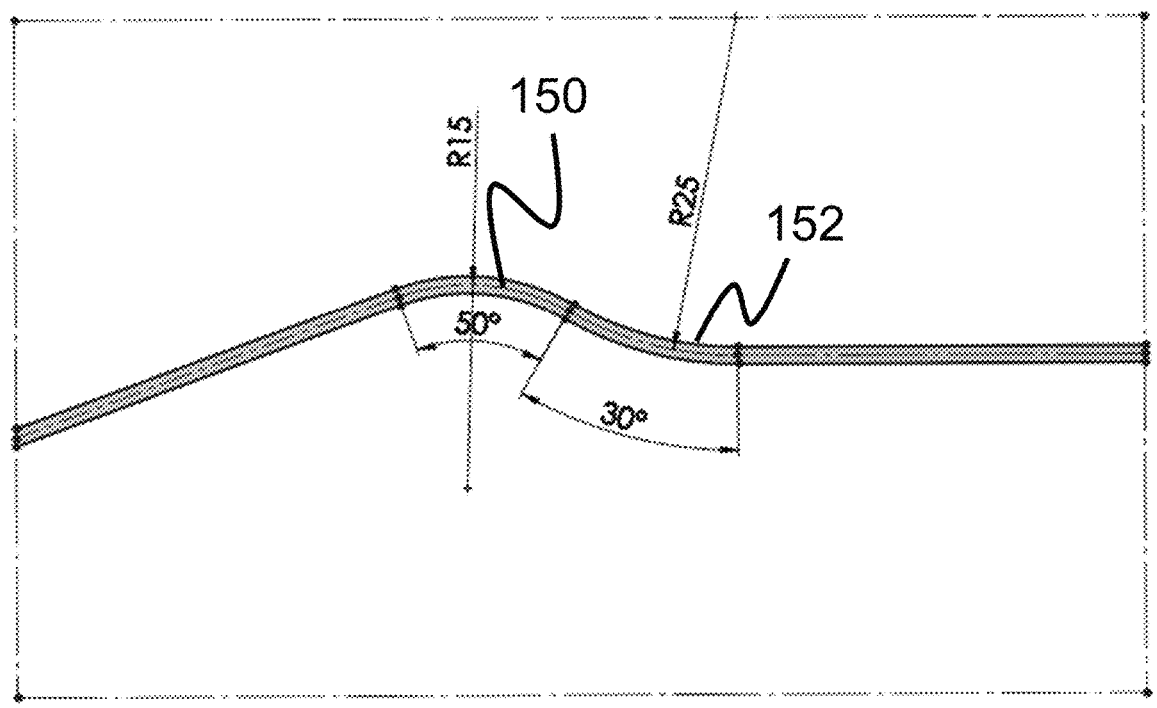
FIG. 15 is an illustration of an alternate configuration of the s-shape curve of the tube, according to one embodiment of the invention.

In the embodiments described and illustrated herein, the curved shape of the tube is pre-shaped into an s-curved design, although other curved shapes may be utilized depending on the degree and length of curvature needed for a particular size and length of the endoscope. FIG. 14 indicates the design parameters of one embodiment of the s-shape tube. The design parameters are set as ($r_1$, $r_2$, α, β)=(15 mm, 25 mm, 30°, 40°) to have the small radius of the motion envelope of 6.28 mm. $\vec{V}_{cam}$ is the unit vector to represent the camera's direction. The initial $\vec{V}_{cam}$, $\vec{V}_{cam,i}$ directs −10.58° respect to +x-axis. The s-curve of the tube 112 includes a distal section 150 with an arc with a central angle of approximately 40 degrees and a radius of curvature of approximately 15 mm and a proximal section 152 with an arc with a central angle of approximately 30 degrees and a radius of curvature of approximately 25 mm. FIG. 15 illustrates an alternate embodiment of the s-curved pattern with the distal section 150 having an arc with a central angle of approximately 50 degrees and a radius of curvature of approximately 15 mm and the proximal section 152 having an arc with a central angle of approximately 30 degrees and a radius of curvature of approximately 25 mm. A diameter of the nitinol tube may range from approximately 0.83 mm-2.15 mm depending on the degree of curvature, size of the overall endoscope and thickness of any coating applied to the tube.

In either embodiment, a minimum radius of curvature of approximately 15 mm and a tube diameter of greater than approximately 1 mm may require a special manufacturing process of: 1) asymmetrically laser-patterning the nitinol tube to have a higher curvature; and 2) shape-setting the deployable arm through a two-step heat treatment.

Figure 16:
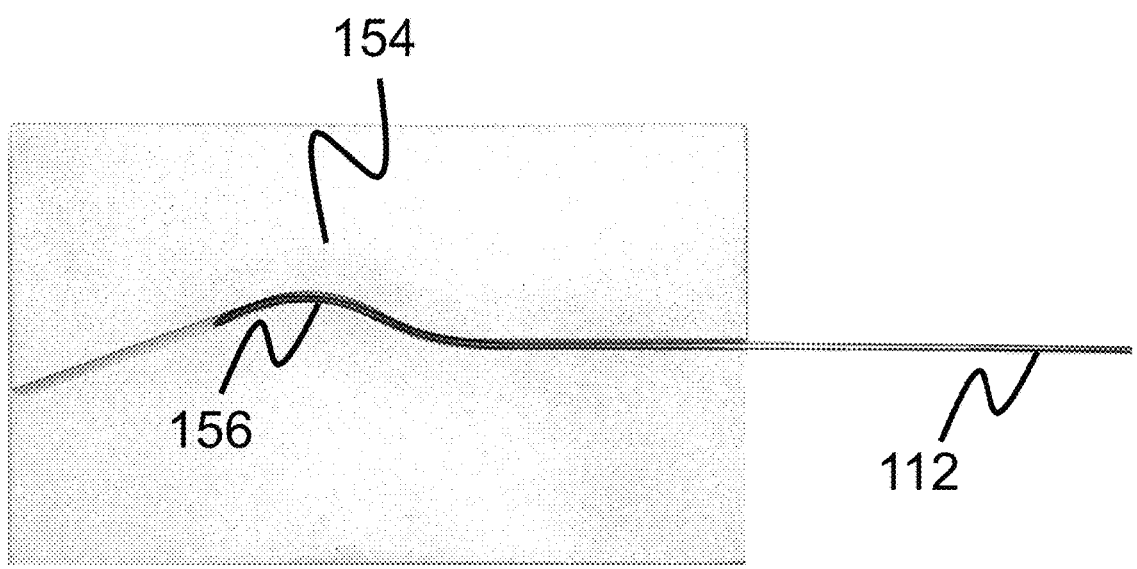
FIG. 16 is an image of an aluminum jig used to set the tube into the pre-deformed s-shape curve during a heat treatment process, according to one embodiment of the invention.

For the shape setting step, an aluminum jig 154 was manufactured, as seen in FIG. 16. The jig 154 is formed with a curved groove 156 and the nitinol tube 112 is then inserted into the groove to undergo the heat treatment. Since the high curvature cannot be shaped by a single heat treatment process, the heat treatment process was performed twice: the first used a low curvature jig (not shown) and the second using the illustrated high curvature jig 154. After the two heat treatment steps, the nitinol tube was shaped into the designated s-curved design. For each heat treatment, the patterned tube was placed in the jig, annealed in the furnace (3-1750, Vulcan Muffle Furnace, Neytech, USA) for approximately 28 minutes at approximately 530° C., and then quenched in room temperature water.

Figure 17:
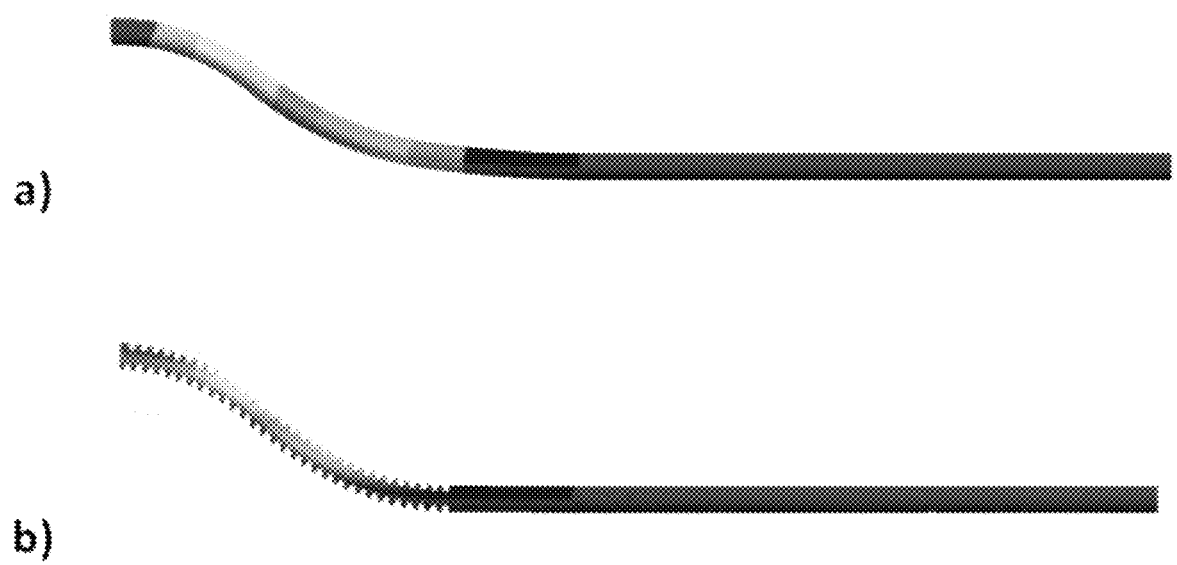
FIG. 17 are images of a finite element methods simulation of the deformation of the tube, according to one embodiment of the invention.

A Finite Element Methods (FEM) simulation was performed to observe the deformation of the deployable tube as the arm advances along the positive x-axis. The rotation about z and x-axes and the deformation along the y-axis were constrained. Two distinguished methods were used for the simulation through ANSYS 2019, USA. In the first method, the patterned part was replaced with the non-patterned tube structure of analytic effective bending stiffness value, as illustrated in FIG. 17 (Simulation A). The calculation of the effective bending stiffness was based on a previous study. In a second method, the patterned tube model was used for analysis, as illustrated in Simulation B. The grey figures represent the undeformed structure at the beginning. The simulation results are compared to the experimental results in the following section.

Figure 18A:
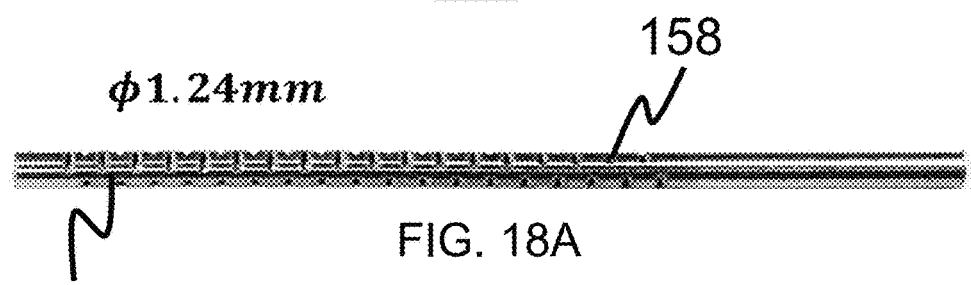
FIG. 18A is an image of the tube with a series of patterned grooves or through-holes disposed on the outer surface thereof, according to one embodiment of the invention.
Figure 18B:
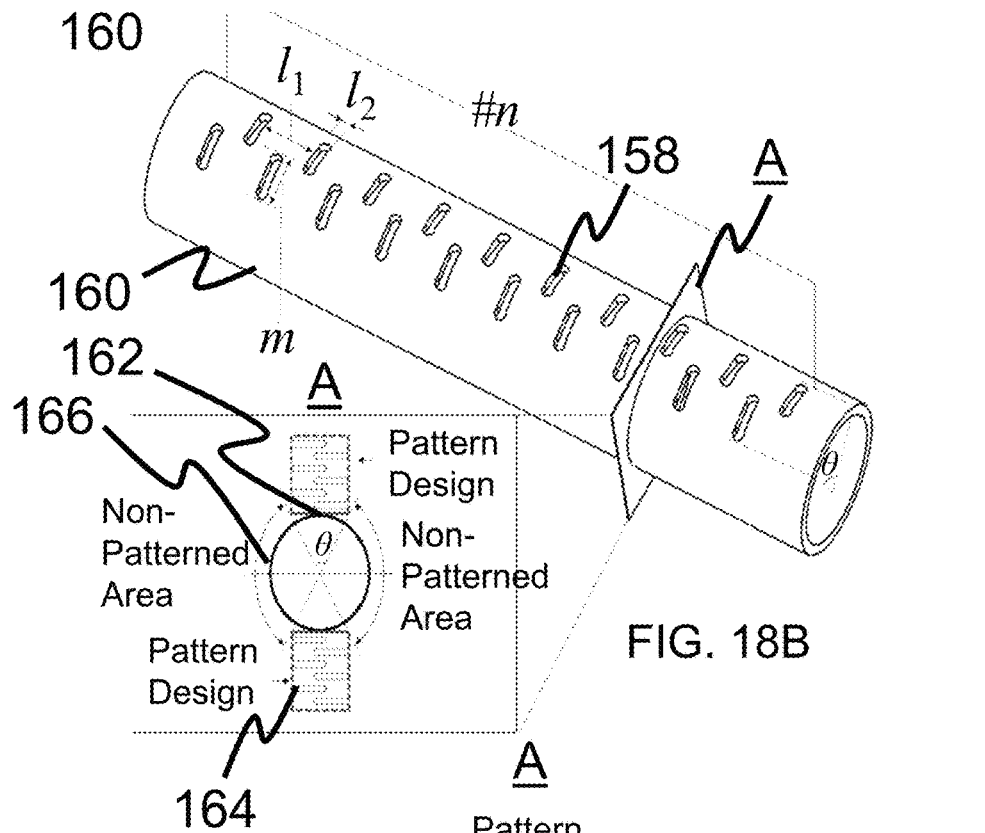
FIG. 18B is a perspective view illustration of the tube illustrating an asymmetric laser pattern disposed on the outer surface thereof, along with a cross-sectional cut-out view of the pattern, according to one embodiment of the invention.
Figure 18C:
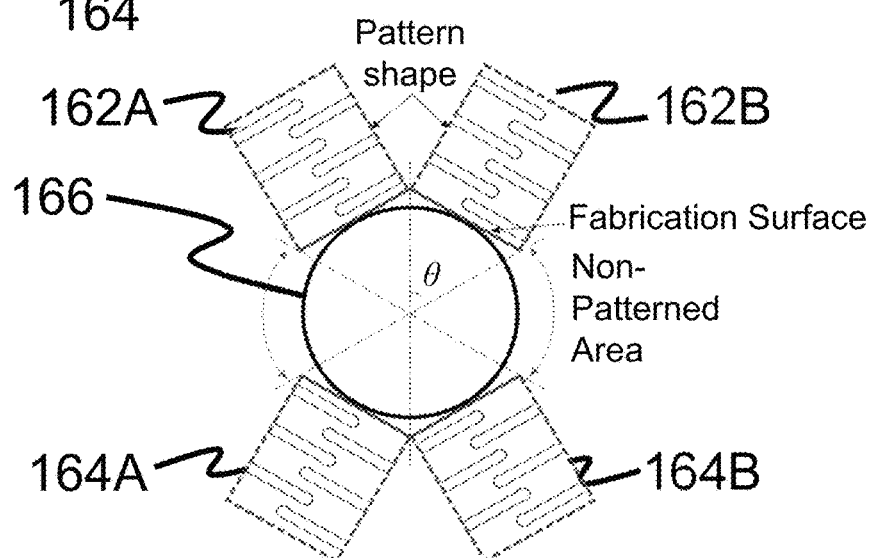
FIG. 18C is a cross-sectional cut-out view of an alternate pattern of grooves or through-holes on the outer surface of the tube, according to one embodiment of the invention.

An image of the tube 112 with asymmetric patterning 158 is shown in FIG. 18A and more clearly illustrated in FIG. 18B. The asymmetric pattern 158 reduces the bending stiffness along the bending direction, so it enables the higher curvature of the tube. At the same time, the asymmetric pattern relatively maintains torsional rigidity and the flexural rigidity along the non-patterned area 160 compared to the universal patterning. A cross-sectional view of the tube 112 is shown in FIG. 18B taken along the A line, which more clearly illustrates a groove or through-hole pattern 158 applied to a top surface 162 of the tube and a bottom surface 164 of the tube while side portions 166 of the tube remain un-patterned. The grooves may penetrate a portion of the thickness of the tube (from approximately ⅓ to ⅔ of the tube thickness) or be formed as through-holes which fully penetrate the tube. FIG. 18C is a cross-sectional cut-out view of an alternate pattern of grooves or through-holes on the outer surface of the tube where a left-top surface 162A and right-top surface 162B are patterned along with a left-bottom surface 164A and right-bottom surface 164B. Each of the patterned surfaces has a central angle of approximately 65 degrees, while the side portions 166 remains un-patterned with a central angle of approximately 50 degrees. Although certain patterns of grooves or through-holes are shown here, a number of asymmetric patterns may be used to achieve the same result of reducing the bend stiffness. Thus, the asymmetrically patterned deployable tube is more stable as it has a higher threshold for buckling, as opposed to the universal patterns.

The groove or through-hole patterns on the nitinol tube were created by laser cutting (RT1000 Laser Tube Cutting Machine, Preco Inc., KS, USA), where feed rate is approximately 127 mm/min, the duty cycle is 12%, power is 250 watts, and pulse frequency is 500 Hz. Through the laser machining and two-step heat treatment, the deployable arm was shaped to the designated design. The arm was assembled with the main shaft and a tool such as graspers and scissors like FIG. 10. The proposed mechanism is well compatible with existing tools of approximately 2 mm or approximately 5 mm diameter.

Figure 19:
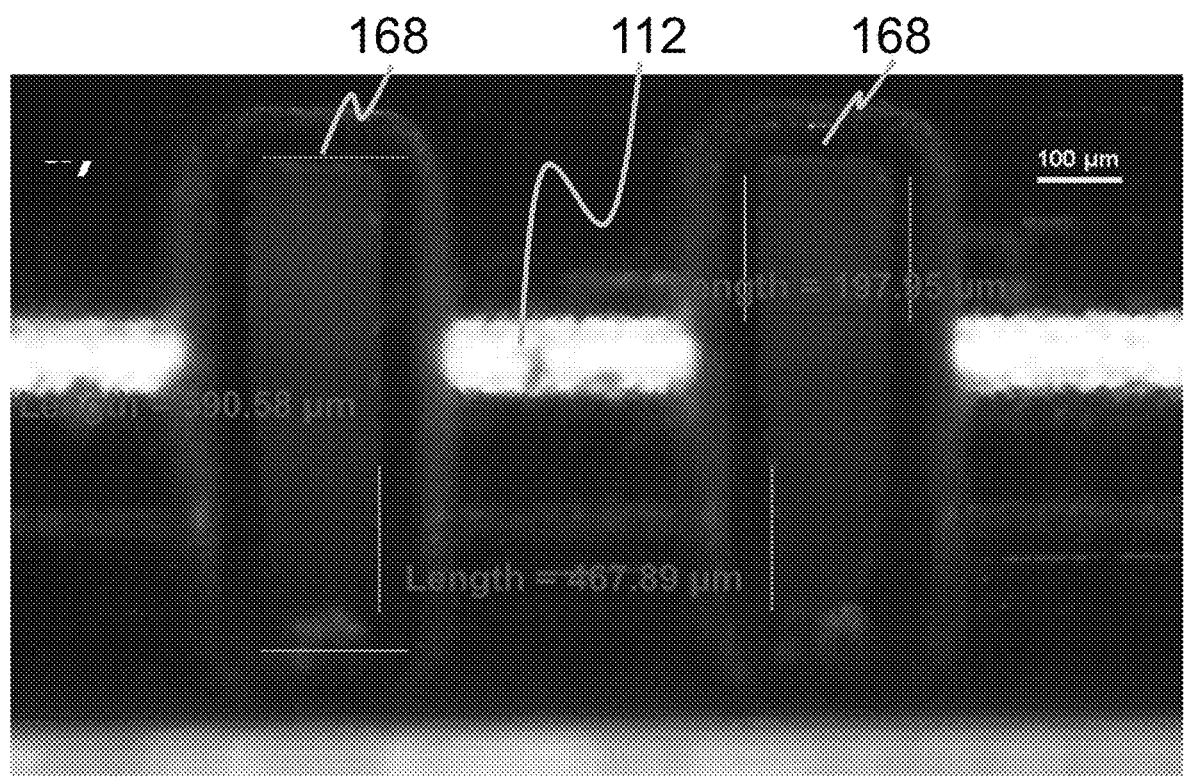
FIG. 19 is a microscopic image of two grooves or through-holes disposed on the outer surface of the tube, according to one embodiment of the invention.
Figure 20:
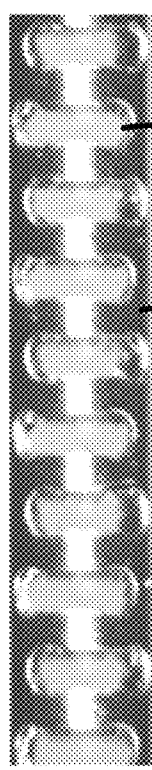
FIG. 20 is a microscopic image of a laser-machined nitinol tube with the asymmetric laser patterning disposed on the outer surface thereof, according to one embodiment of the invention.
Figure 21:
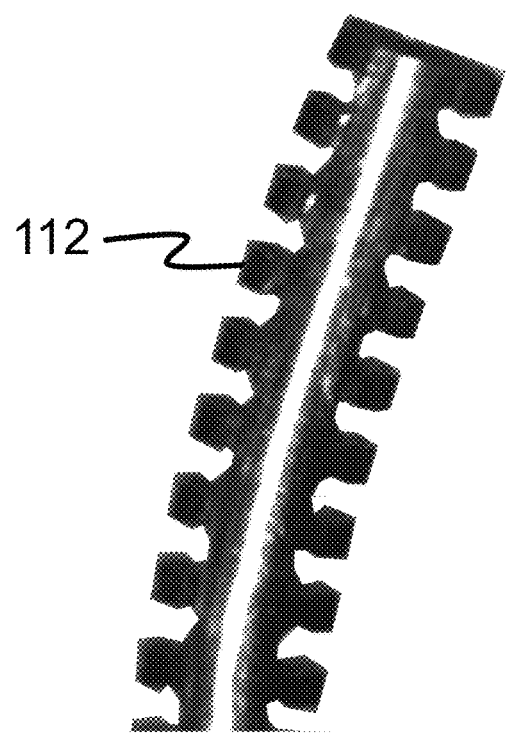
FIG. 21 is a microscopic image of a laser-machined nitinol tube after the heat treatment process, according to one embodiment of the invention.
Figure 22A:
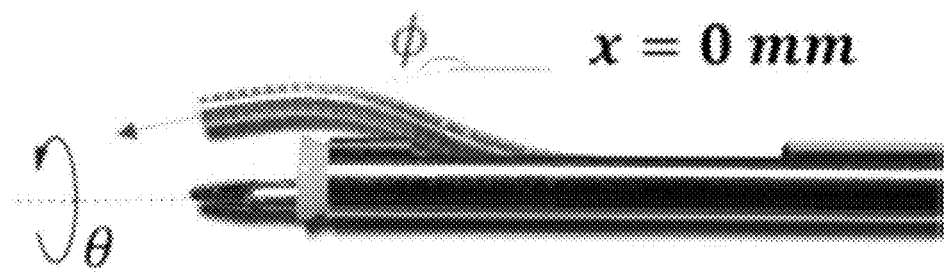
FIG. 22A-22D are side-view images of the deployed tooltip camera at different translated distances to illustrate a range of directions of the camera due to translational movement, according to one embodiment of the invention.
Figure 22B:
Figure 22C:
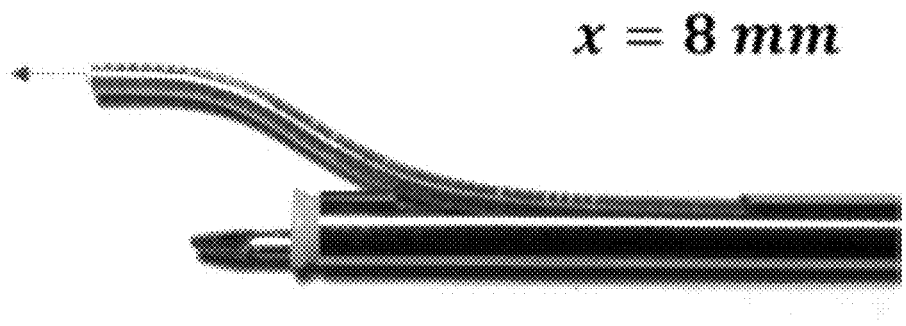
Figure 22D:
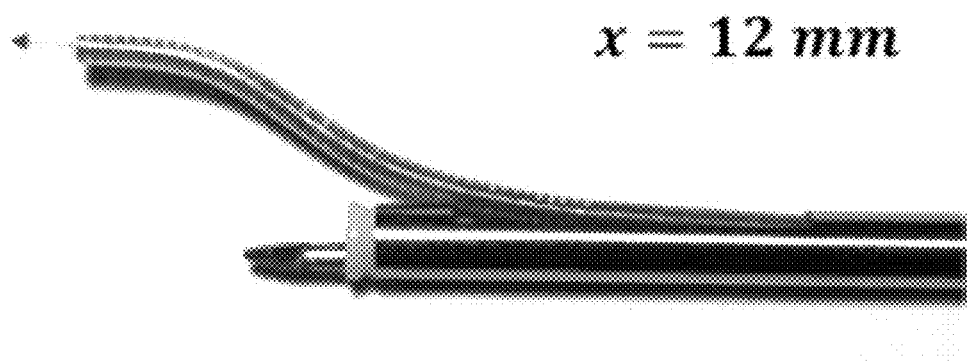

FIG. 19 is a microscopic image of two grooves or through-holes 168 disposed on the outer surface of the tube, where the dimensions of each through hole is approximately 0.2 mm×0.6 mm, with a spacing of approximately 0.5 mm between each through hole. FIG. 20 is a microscopic image of a laser-machined nitinol tube 112 with the asymmetric laser patterning 168 disposed on the outer surface thereof, and FIG. 21 is a microscopic image of a laser-machined nitinol tube 112 after the heat treatment process illustrating the pre-deformed shape of the heat-treated tube.

The tendon-pulley mechanism is relatively complicated to be scaled down and phase changing mechanism takes time to switch states. The tooltip camera does not need axillary actuators or bulky structures. The tube's rotational and translational movements can be controlled at the proximal side by motors or manually. Its simple and intuitive design ease the difficulties of assembling in a smaller dimension.

In addition, surgeons emphasize that monitoring the 360° view with respect to the end effector helps them to recognize the target tissue exactly during surgical manipulation. However, when it advances through the same entrance port (i.e. trocar) of the major tool, conventional fixed endoscopes hardly offer the view below the end effector in SLS. The proposed wrist is deployed from the sideway of the main shaft. The wrist is translated, rotated, and bent to change the field of view (FOV) to reduce the unreachable area. In the experiment, the wrist offers 97.8 degrees of independent roll motion and 18.9 degrees of pitch motion. It is expected to contribute to reducing the unreachable area in SLS or the need for multiple ports to minimize invasiveness.

All materials are biocompatible and sterilizable: the main shaft of stainless steel, the deployable arm of nitinol, the PDMS coatings. The connecting parts can be replaced by stainless steel or titanium. In terms of cost, the nitinol is the most expensive material in this mechanism. Alternatively, the deployable arm can consist of the curved nitinol part and the straight stainless steel part to reduce costs. The two parts can be connected to each other by laser welding.

The tube can be used for laser ablation as well as endoscopy, and the wrist can be utilized for delivering the triangularization of SLS. Due to a lack of scalable and highly articulated tubes, triangularization has been technical hurdles in SLS. Its pre-shaped curvature is high and adjusts its curvature by bending. As illustrated in FIG. 22A-22D, we plan to employ the two s-curved wrists for both left and right controllers. The wrists keep straight when they are restored at the main shaft. When advanced and deployed, they can form triangularization using their s-curved structure. In addition, the 6-DOF controller will be utilized to integrate with other tubular mechanisms.

It is contemplated that additional applications may be possible using a three-dimensional (3D) curved shape. The current design of the deployable arm is based on an s-curved shape in 2D. Three-dimensionally curved design allows flexibility in customizing workspace and the sweeping volume of the tube. Thanks to its simple mechanism and scalability, the tube will be applicable to microsurgical applications.

Electromagnetic Tracking Test on the Deployable Wrist

The motorized control system was set up to examine 2-DOF motion control of deployable wrist by 1) controlling the FOV, and 2) repeating the full retraction and deployment of the arm. The wrist is held by the collet chuck and the motorized stage controls the rotational and translational movement of the wrist. Each controller has 3 rotational and 3 translational stages and the user controls the stages by stylus pen of the 3D haptic device (Geomagic touch, 3D systems, USA) or commanding joint degree values of each stage.

The electromagnetic tracking experiment was performed to examine the direction of the distal tip. The 5-DOF electromagnetic needle sensor was equipped at the distal tip of the deployable arm. The electromagnetic tracking system (Aurora, Northern Digital, Waterloo, ON, Canada) was installed to track the sensor. The direction of the sensor was synchronized with the direction of the distal tip. The direction and the position of the distal tip are determined by the rotational and translational movement of the arm.

At first, the direction was measured while the tube undergoes translational and rotational movement. The tube was translated from 0 mm, 4 mm, 8 mm and 12 mm, as illustrated in FIGS. 22A-22D, respectively. The rotational range of the tube is determined by the pattern hole of the main shaft. The range of the roll movement is from 41.1° to 138.9°. Direction measurement was repeated for $x \in \{0, 2$ mm, 4 mm, 6 mm, 8 mm, 10 mm, 12 mm$\}$ and the roll angle, $\theta \subset \{45°, 60°, 75°, 90°, 105°, 120°, 135°\}$, summing up 49 cases. The direction measurement was repeated five times and the average value was taken for each case. The average standard deviation is 2.37° for the 49 cases. Table 1 demonstrates the results of the direction of the tube.

retraction and the deployment was repeated using the aforementioned setup, and the he translational stage holding the tube repeatedly moved back and forth from 0 to 12 mm. The tube was functional and did not exhibit failure even after repetitive testing up to 450 cycles.

Methods of Assembly

Figure 24:
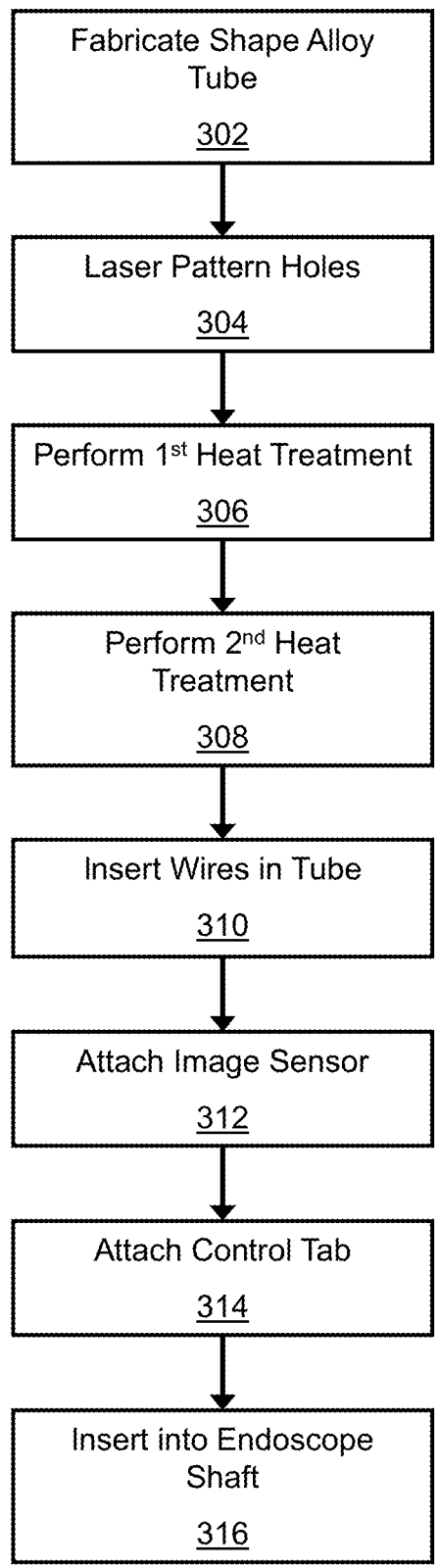
FIG. 24 is a flow diagram illustrating an example process for manufacturing an endoscope with the tooltip camera, according to an embodiment of the invention.

FIG. 24 is a flow diagram illustrating an example process for manufacturing an endoscope with the tooltip camera, according to an embodiment of the invention. A shape alloy tube 302 is fabricated, after which a series of asymmetrically-patterned holes are patterned into the tube surface in step 304. In step 306, a first heat treatment is applied to the tube to create a first degree of curvature. In step 308, a second heat treatment is applied to create a second degree of curvature. After the tube has been fabricated, the wires for the camera are inserted through the tube in step 310 and the image sensor is attached at the distal tip in step 312. The control tab is then secured to the proximal end of the tube in step 314, after which the tooltip camera is inserted into the endoscope shaft in step 316.

The Phantom Test of Single-Port Laparoscopic Surgery

The goal of this test is to examine the nearby environments and monitor the surroundings of the end effector for safe and minimally invasive operations. In the test, we integrated the 5 mm-diameter graspers (Endopath, Ethicon

TABLE I

The direction of the wrist's distal tip measured by EM tracker:

| $\theta, \phi$ | 45° | 60° | 75° | 90° | 105° | 120° | 135° |
|---|---|---|---|---|---|---|---|
| 0 mm | 45.1°, 190.6° | 59.7°, 189.3 | 75.5°, 188.9° | 91.2°, 192.5° | 106.1°, 190.0° | 120.5°, 189.4° | 134.3°, 189.2° |
| 2 mm | 46.0°, 186.6° | 61.2°, 184.7 | 73.7°, 184.6° | 89.6°, 184.5° | 106.0°, 188.3° | 119.6°, 185.3° | 136.4°, 188.8° |
| 4 mm | 44.3°, 185.9° | 58.6°, 186.1 | 74.2°, 184.0° | 90.5°, 182.9° | 103.9°, 184.6° | 118.7°, 184.0° | 133.7°, 182.8° |
| 6 mm | 45.5°, 180.2° | 59.7°, 183.2 | 75.7°, 183.8° | 91.0°, 183.0° | 104.1°, 181.9° | 120.7°, 181.3° | 136.2°, 180.6° |
| 8 mm | 45.4°, 180.5° | 58.7°, 178.0 | 74.7°, 179.3° | 89.4°, 179.9° | 104.9°, 178.0° | 120.4°, 178.0° | 134.7°, 176.6° |
| 10 mm | 44.2°, 178.5° | 59.6°, 177.8 | 75.3°, 175.2° | 88.9°, 178.9° | 104.2°, 178.7° | 118.9°, 175.0° | 134.3°, 177.5° |
| 12 mm | 45.3°, 175.2° | 60.1°, 173.9 | 73.8°, 172.1° | 91.0°, 173.8° | 104.2°, 173.5° | 120.8°, 173.5° | 135.0°, 174.7° |

The experimental results when $\theta=90°$ are compared with the simulation data in Table II.

endo-surgery, USA) to our proposed wrist and explored through the laparoscopic training box. We put uneven terrain

TABLE II

The comparison between experiment and simulation results on the wrist's bending direction:

| x | 0 mm | 2 mm | 4 mm | 8 mm | 10 mm | 12 mm |
|---|---|---|---|---|---|---|
| Simulation A | 190.2° (2.3) | 182.2° (2.3) | 179.5° (3.4) | 178.5° (4.5) | 172.3° (7.6) | 164.5° (0.1) |
| Simulation B | 190.2° (2.3) | 179.2° (5.8) | 176.7° (6.2) | 174.2° (8.8) | 169.9° (10.0) | 160.2° (13.4) |
| Experiment | 192.5° | 184.5° | 182.9° | 183.0° | 179.9° | 173.6° |

The effective bending stiffness model showed more consistency with the experimental results. The red number in Table II indicates the error of the simulation results compared to experimental results. The average errors for simulation A and B are 4.87 and 7.67 degrees, respectively. The error increases as the tube advances further (x value increases).

Figure 23:
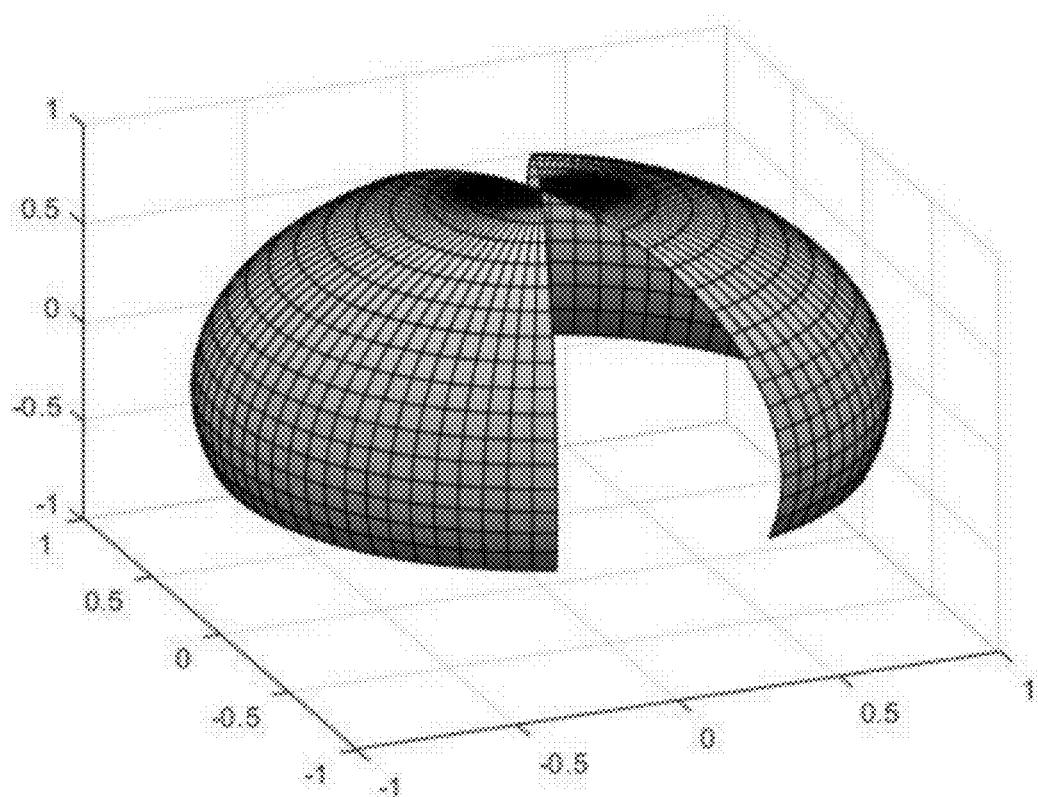
FIG. 23 is a field of view (FOV) diagram of the tooltip camera illustrating an FOV of the tooltip camera over a range of translational movement and rotational movement, according to one embodiment of the invention.

FIG. 23 illustrates a field of view (FOV) diagram of the proposed tube with the equipped camera that has 120 degrees FOV. The diagram assumes the main shift fixed and only considers the movement of the wrist. The expanded FOV was tested in the phantom test of the following section. Secondly, the tube was fully pulled back to be restored inside of the main shaft and then deployed again. The in the training box, aimed to grasp target tissue with proper visual feedback, and we used single port access during the test. In the test, using the deployable endoscopic wrist, we accordingly adjusted the view angle when the view is obstructed. The endoscope at the wrist's distal tip offers a detail view of the end-effector and its surroundings. The 1 Mpixel high resolution of camera view lets users distinguish nearby tissues clearly. Three surgeons validated that the mechanism offered proper endoscopic visual feedbacks. In SLS, the area under the tooltip can be blind spots, but the proposed mechanism can monitor the underneath area and safely identify the target tissue.

System for Performing Endoscopy

Figure 25:
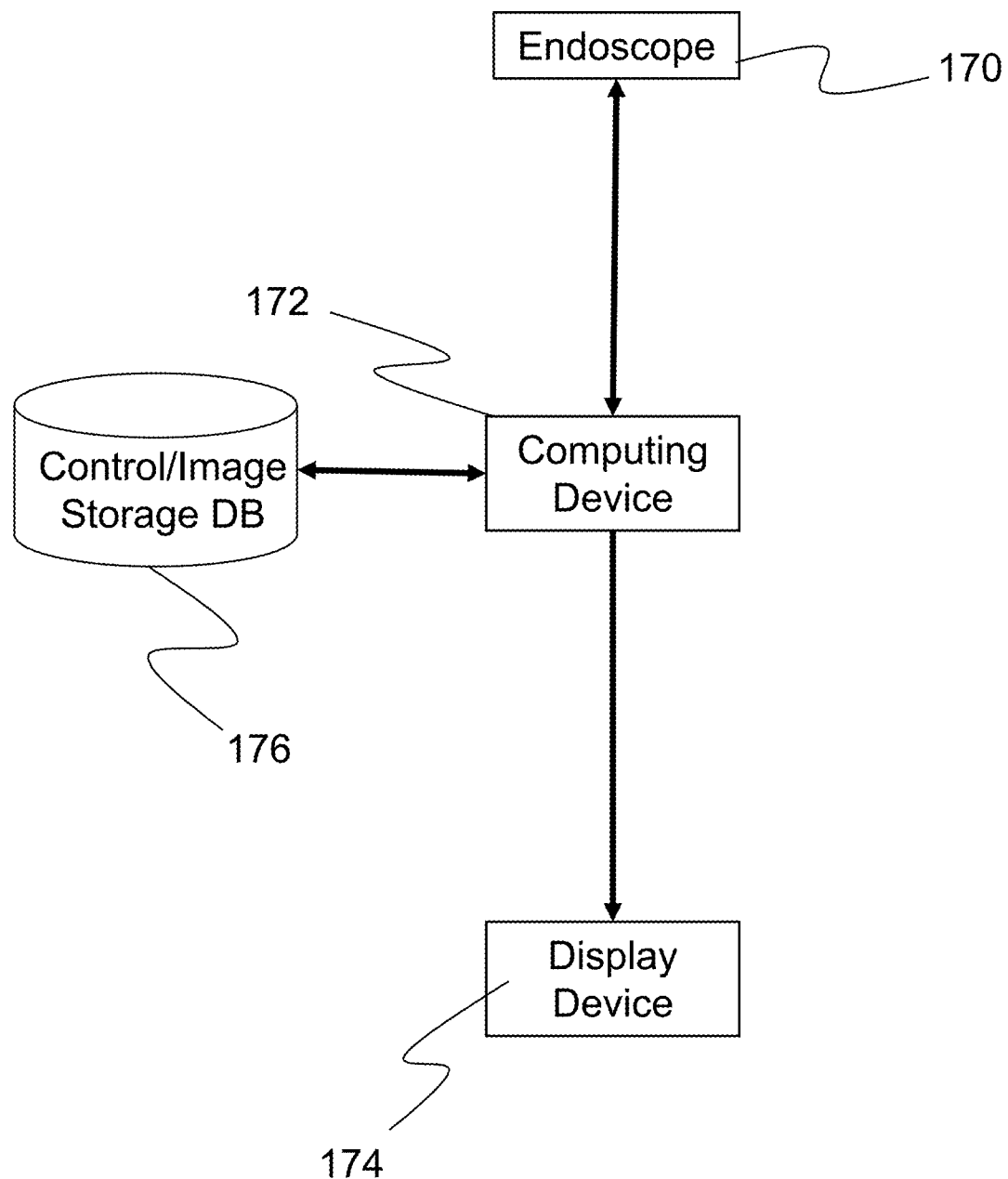
FIG. 25 is a block diagram illustrating an example system for performing an endoscopic procedure that may be used in connection with the various embodiments described herein.

FIG. 25 is a block diagram illustrating an example system for performing an endoscopic procedure that may be used in connection with the various embodiments described herein. The endoscope 170 may be connected with a computing device 172 which receives the images captured by the tooltip camera on the endoscope and passes them on to a display device 174 to display the images to an operator performing the procedure. In one embodiment, the images may also be transmitted from the computing device to a control/image storage database 176 for storing of the images for future viewing and analysis. The computing device 172 may also utilize one or more software and hardware components to enhance or manipulate the images or a user interface to display to the operator to improve the viewability or understanding of the images. These software components may be stored on the control/image storage database 176 as well.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An endoscope comprising:
   a hollow shaft with a proximal end and a distal end; and
   an image capture device disposed within the shaft, the image capture device comprising:
   a tube pre-deformed in a substantially curved shape but configured to have a substantially linear shape within the shaft, wherein the tube comprises a shape memory alloy; and
   an image sensor disposed on a distal tip of the tube;
   wherein a distal portion of the tube is configured to deploy from a slot-shaped opening in a side portion of the hollow shaft along a longitudinal axis of the hollow shaft into a deployed position in which the tube assumes the substantially curved shape, and wherein the deployed tube may be rotated about the longitudinal axis.

2. The endoscope of claim 1, further comprising a tool configured to pass through the shaft and having a tooltip configured to protrude having a tooltip protruding from the distal end of the shaft.

3. The endoscope of claim 2, wherein the tube is configured to change from the linear shape to the curved shape upon translation of the tube through the opening in the shaft.

4. The endoscope of claim 1, wherein movement of the tube is configured to be controlled at a proximal portion via direct manual control or electro-mechanical control.

5. The endoscope of claim 1, wherein the tube is patterned with a series of grooves or holes.

6. The endoscope of claim 1, wherein the substantially curved shape is an s-shape.

7. The endoscope of claim 6, wherein the s-shape includes a proximal arc with a central angle of approximately 30 degrees and a distal arc with a central angle of approximately 40 degrees.

8. The endoscope of claim 1, wherein the image capture device further comprises a light source disposed on the distal tip of the tube which is connected with an LED-based fiber disposed along a length of the tube.

9. The endoscope of claim 1, wherein the image sensor is connected with a power source and an image processing device via at least one wire disposed inside a length of the tube.

10. A method of viewing an endoscopic tool during an endoscopic procedure, comprising the steps of:
    inserting a distal end of an endoscope into a body cavity, wherein the endoscope is a hollow shaft enclosing an image capture device and the endoscopic tool, and wherein the image capture device comprises:
    a tube pre-deformed in a substantially curved shape but configured to have a substantially linear shape within the shaft wherein the tube comprises a shape memory alloy; and
    an image sensor disposed on a distal tip of the tube; and
    deploying a distal portion of the tube with the image capture device into the body cavity from a slot-shaped opening in a side portion of the hollow shaft along a longitudinal axis of the hollow shaft in which the tube assumes the substantially curved shape, and wherein the deployed tube may be rotated about the longitudinal axis.

11. The method of claim 10, further comprising extending a tooltip of the endoscopic tool into the body cavity from a distal tip of the shaft.

12. The method of claim 10, further comprising deploying the image capture device to provide a rear perspective view of the endoscopic procedure.

13. The method of claim 10, further comprising deploying the image capture device into an s-shape.

* * * * *